United States Patent [19]
Phillips et al.

[11] Patent Number: 6,166,060
[45] Date of Patent: Dec. 26, 2000

[54] 1H-4(5)-SUBSTITUTED IMIDAZOLE DERIVATIVES

[75] Inventors: James G. Phillips, Bay Village; Clark E. Tedford, South Russell, both of Ohio; Nishith C. Chaturvedi, Gujarat, India; Syed M. Ali, Solon, Ohio

[73] Assignee: Gliatech, Inc., Cleveland, Ohio

[21] Appl. No.: 08/948,801

[22] Filed: Oct. 10, 1997

Related U.S. Application Data

[63] Continuation-in-part of application No. 08/913,091, filed as application No. PCT/US96/07873, May 29, 1996, which is a continuation-in-part of application No. 08/454,522, May 30, 1995, abandoned.

[51] Int. Cl.[7] ............... A61K 31/417; A61K 31/4174; C07D 233/64
[52] U.S. Cl. ............... 514/400; 514/396; 548/335.1; 548/335.5; 548/341.1; 548/346.1
[58] Field of Search .............. 548/335.1, 335.5, 548/341.1, 346.1; 514/396, 400

[56] References Cited

U.S. PATENT DOCUMENTS

| | | |
|---|---|---|
| 4,517,198 | 5/1985 | Kurkela et al. . |
| 4,568,686 | 2/1986 | Karjalainen et al. ............... 514/396 |
| 4,707,487 | 11/1987 | Arrang et al. . |
| 5,010,095 | 4/1991 | Sterk et al. . |
| 5,173,502 | 12/1992 | Malen et al. . |
| 5,217,986 | 6/1993 | Pomponi et al. . |
| 5,248,689 | 9/1993 | Girard et al. . |
| 5,290,790 | 3/1994 | Arrang et al. . |
| 5,559,113 | 9/1996 | Schwartz et al. ............... 514/252 |

FOREIGN PATENT DOCUMENTS

| | | |
|---|---|---|
| WO 92/15567 | 9/1992 | WIPO . |
| WO 93/14070 | 6/1993 | WIPO . |
| WO 95/12581 | 5/1995 | WIPO . |

OTHER PUBLICATIONS (Schwartz, 1975) *Life Sci. 1.7*: 503–518.
(Inagaki et al., 1988) *J. Comp. Neurol. 273*: 283–300.
(Schwartz et al., 1986) *TIPS 8*: 24–28.
Babizhayel et al., "Pseudodipeptide product, etc.", CA 123:286746 (1995).

*Primary Examiner*—Patricia L. Morris
*Attorney, Agent, or Firm*—Rockey, Milnamow & Katz, Ltd.

[57] ABSTRACT

The present invention provides, in its principal aspect, compounds of the general formula:

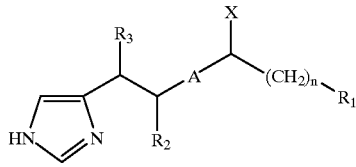

(1.0)

when

A is —NHCO—, —N(CH$_3$)—CO—, —NHCH$_2$—, —N(CH$_3$)—CH$_2$—, —CH=CH—, —COCH$_2$—, CH$_2$CH$_2$—, —CH(OH)CH$_2$— or —C≡C—;

X can be H, CH$_3$, NH$_2$, NH(CH$_3$),N(CH$_3$)$_2$, OH, OCH$_3$, SH,

R$_2$ is hydrogen or a methyl or ethyl group;

R$_3$ is hydrogen or a methyl or ethyl group;

n is 0, 1, 2, 3, 4, 5 or 6;

R$_1$ is selected from the group consisting of (a) alkyl; (b) C$_3$ to C$_8$ cycloalkyl; (c) phenyl or substituted phenyl; (d) heteroocyclic; and (f) decahydronaphthalene or octahydroindane; and When R$_1$ and X taken together denote a 5, 6 or 6, 6 saturated bicyclic ring structure, X can be NH, O, S, SO$_2$, When X is constrained in a 5, 6 or 6, 6, saturated bicyclic ring structure, then for example, when X=NH, R$_1$ and X taken together mean an octahydroindole ring structure directly attached to A.

24 Claims, No Drawings

1H-4(5)-SUBSTITUTED IMIDAZOLE DERIVATIVES

CROSS REFERENCE TO RELATED APPLICATIONS

This application is a continuation-in-part of patent application U.S. Ser. No. 08/913,091 filed Sep. 5, 1997, (the U.S. national phase application of PCT application PCT/US96/07873, filed May 29, 1996, which is a continuation-in-part of U.S. Ser. No. 08/454,522, filed May 30, 1995, now abandoned.

TECHNICAL FIELD

This invention relates to compounds having pharmacological activity, to compositions containing these compounds, and to a medical method of treatment employing the compounds and compositions. More particularly, this invention concerns certain 1H-4(5)-substituted imidazole derivatives and their salts or solvates. These compounds have $H_3$ histamine receptor antagonist activity. This invention also relates to pharmaceutical compositions containing these compounds, and to a method of treating disorders in which histamine $H_3$ receptor blockade is beneficial.

BACKGROUND OF THE INVENTION

Histamine is a chemical messenger involved in various complex biological actions. When released, histamine interacts with specific macromolecular receptors on the cell surface or within a target cell to elicit changes in many different bodily functions. Various cell types including smooth muscle, blood cells, cells of the immune system, endocrine and exocrine cells as well as neurons respond to histamine by stimulating the formation of intracellular signals, including formation of phosphatidylinositol or adenylate cyclase. Evidence that histamine plays a role as a neurotransmitter was established by the mid to late 1970's (Schwartz, 1975) *Life Sci.* 17: 503–518. Immunohistochemical studies identified histaminergic cell bodies in the tuberomammillary nucleus of the posterior hypothalamus with widespread projections in the dicencephalon and telencephalon (Inagaki et al., 1988) *J. Comp. Neurol.* 273: 283–300.

Identification of two histamine receptors ($H_1$ and $H_2$) was reported to mediate the biochemical actions of histamine on neurons. Recently, studies have demonstrated the existence of a third subtype of histamine receptor, the histamine $H_3$ receptor (Schwartz et al., 1986) *TIPS* 8: 24–28. Various studies have now demonstrated that histamine $H_3$ receptors are found on the histaminergic nerve terminals in the brains of several species, including man (Arrang et al., 1983) *Nature* 302: 832–837. The $H_3$ receptor found on the histaminergic nerve terminal was defined as an autoreceptor and could intimately control the amount of histamine released from the neurons. Histamine, the natural compound, was capable of stimulating this autoreceptor but when tested against known $H_1$ and $H_2$ receptor agonists and antagonists, a distinct pharmacological profile emerged. Further, $H_3$ receptors have been identified on cholinergic, serotoninergic and monoamine nerve terminals in the peripheral nervous system (PNS) and central nervous system including the cerebral cortex and cerebral vessels. These observations suggest that $H_3$ receptors are uniquely located to modulate histamine as well as other neurotransmitter release, and $H_3$ antagonists could be important mediators of neuronal activity.

As stated, CNS histaminergic cell bodies are found in the magnocellular nuclei of the hypothalamic mammillary region and these neurons project diffusely to large areas of the forebrain. The presence of histaminergic cell bodies in the tuberomamillary nucleus of the posterior hypothalamus, a brain area involved in the maintenance of wakefulness, and their projections to the cerebral cortex suggest a role in modulating the arousal state or sleep-wake. The histaminergic projection to many limbic structures such as the hippocampal formation and the amygdaloid complex suggest roles in functions such as autonomic regulation, control of emotions and motivated behaviors, and memory processes.

The concept that histamine is important for the state of arousal, as suggested by the location of histaminergic pathways, is supported by other types of evidence. Lesions of the posterior hypothalamus is well known to produce sleep. Neurochemical and electrophysiological studies have also indicated that the activity of histaminergic neurons is maximal during periods of wakefulness and is suppressed by barbiturates and other hypnotics. Intraventricular histamine induces the appearances of an arousal EEG pattern in rabbits and increased spontaneous locomotor activity, grooming and exploratory behavior in both saline and pentobarbital-treated rats.

In contrast, a highly selective inhibitor of histidine decarboxylase, the sole enzyme responsible for histamine synthesis, has been shown to impair waking in rats. These data support the hypothesis that histamine may function in modulating behavioral arousal. The role of the $H_3$ receptor in sleep-waking parameters has been recently demonstrated (Lin et al., 1990) *Brain Res.* 529: 325–330. Oral administration of RAMHA, a $H_3$ agonist, caused a significant increase in deep slow wave sleep in the cat. Conversely, thioperamide, a $H_3$ antagonist, enhanced wakefulness in a dose-dependent fashion. Thioperamide has also been shown to increase wakefulness and decrease slow wave and REM sleep in rats. These findings are consistent with in vivo studies demonstrating that thioperamide caused an increase in synthesis and release of histamine. Together, these data demonstrate that selective $H_3$ antagonists may be useful in the treatment of arousal states and sleep disorders.

Serotonin, histamine, and acetylcholine have all been demonstrated to be diminished in the Alzheimer's (AD) brain. The histamine $H_3$ receptor has been demonstrated to regulate the release of each of these neurotransmitters. An $H_3$ receptor antagonist would therefore be expected to increase the release of these neurotransmitters in brain. Since histamine has been demonstrated to be important in arousal and vigilance, $H_3$ receptor antagonists might enhance arousal and vigilance via increasing levels of neurotransmitter release and improve cognition. Thus, the use of $H_3$ receptor antagonists in AD, attention deficit hyperactive disorders (ADHD), age-related memory dysfunction and other cognitive disorders would be supported.

$H_3$ receptor antagonists may be useful in treating several other CNS disorders. It has been suggested that histamine may be involved in the control of sleep/wake states as well as states of arousal and alertness, cerebral circulation, energy metabolism, and hypothalmic hormone secretion. Recent evidence has indicated the possible use of $H_3$ antagonists in the treatment of epilepsy. Work has demonstrated an inverse correlation between the duration of clonic convulsions and brain histamine levels. Thioperamide, a $H_3$ antagonist, was also shown to significantly and dose-dependently decrease the durations of every convulsive phase after electrically-induced convulsions and increase the electroconvulsive threshold.

In spite of their low density, $H_3$ receptor binding sites can be detected outside the brain. Several studies have revealed the presence of $H_3$ heteroreceptors in the gastrointestinal tract, as well as upon neurons of the respiratory tract. Accordingly, an $H_3$ receptor antagonist may be useful in the treatment of diseases and conditions such as asthma, rhinitis, airway congestion, inflammation, hyper and hypo motility and acid secretion of the gastrointestinal tract. Peripheral or central blockade of $H_3$ receptors may also contribute to changes in blood pressure, heart rate and cardiovascular output and could be used in the treatment of cardiovascular diseases.

U.S. Pat. No. 4,707,487 discloses compounds of the general formula:

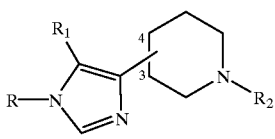

in which $R_1$ denotes H, $CH_3$, or $C_2H_5$, R denotes H or $R_2$ and $R_2$ denotes an alkyl, piperonyl, 3-(1-benzimidazolonyl)-propyl group; a group of formula:

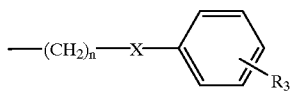

in which n is 0, 1, 2, or 3, X is a single bond or alternatively —O—, —S—, —NH—, —CO—, —CH=CH— or

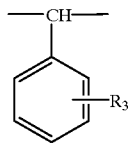

and $R_3$ is H, $CH_3$, F, CN or an acyl group; or alternatively a group of formula:

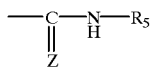

in which Z denotes an O or S atom or a divalent group NH, N—$CH_3$, or N—CN, and $R_5$ denotes an alkyl group, a cycloalkyl group which can bear a phenyl substituent, a phenyl group which can bear a $CH_3$ or F substituent, a phenylalkyl ($C_1$–$C_3$) group or a naphthyl, adamantyl, or p-toluenesulphonylgroup. It is also disclosed that these compounds antagonize the histamine $H_3$ receptors and increase the rate of renewal of cerebral histamine.

WO 92/15567 discloses compounds of general formula:

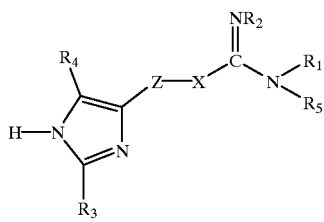

wherein: Z is a group of formula $(CH_2)_m$, wherein m=1–5 or a group of the formula:

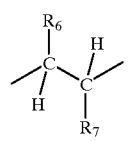

wherein $R_6$=($C_1$–$C_3$) alkyl, $R_7$=($C_1$–$C_3$) alkyl; X represents S, NH, or $CH_2$; $R_1$ represents hydrogen, ($C_1$–$C_3$) alkyl-, aryl ($C_1$–$C_{10}$) alkyl-, wherein aryl may optionally be substituted, aryl, ($C_5$–$C_7$) cycloalkyl, ($C_1$–$C_{10}$) alkyl-, or a group of the formula:

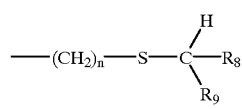

wherein n=1–4, $R_8$ is aryl, aryl ($C_1$–$C_{10}$) alkyl-, ($C_5$–$C_7$) cycloalkyl- or ($C_5$–$C_7$) cycloalkyl ($C_1$–$C_{10}$) alkyl-, and $R_9$ is hydrogen, ($C_1$–$C_{10}$) alkyl- or aryl; $R_2$ and $R_5$ represent hydrogen, ($C_1$–$C_3$) alkyl-, aryl or arylalkyl-, wherein aryl may optionally be substituted; $R_3$ represents hydrogen, ($C_1$–$C_3$) alkyl, aryl, or arylalkyl-, wherein aryl may be substituted; and $R_4$ represents hydrogen, amino-, nitro-, cyano-, halogen-, ($C_1$–$C_3$) alkyl, aryl, or arylalkyl-, wherein aryl may optionally be substituted; wherein aryl is phenyl, substituted phenyl, naphthyl, substituted naphthyl, pyridyl or substituted pyridyl. These compounds are reported to have agonistic or antagonistic activity on the histamine $H_3$ receptor.

U.S. Pat. No. 5,217,986 discloses compound of formula:

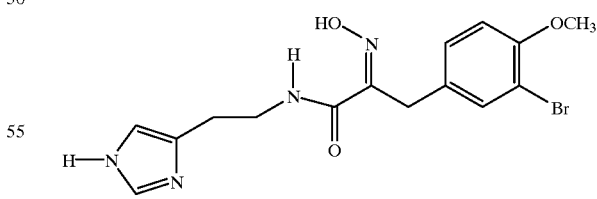

This compound is reported to be active in an $H_3$ receptor assay, is reported to be an $H_3$ antagonist on guinea pig ileum, and accordingly is said to be useful in the treatment of diseases and conditions such as asthma, rhinitis, airway congestion, inflammation, cardiac arrhythmias, hypertension, hyper and hypo motility and acid secretion of the gastrointestinal tract, hypo- and hyper-activity of the central nervous system, migraine, and glaucoma.

WO 93/14070 discloses compounds of general formula:

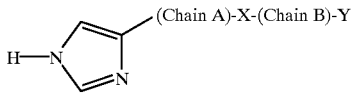

IA

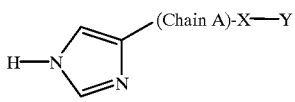

IB

Chain A represents a hydrocarbon chain, saturated or unsaturated, of 1–6 carbon atoms in length; X represents —O—, —S—, —NH—, —NHCO—, —N(alkyl)CO—, —NHCONH—, —NH—CS—NH—, —NHCS—, —O—CO—, —CO—O—, —OCONH—, —OCON (alkyl)—, —OCONH—CO—, —CONH—, —CON (alkyl)—, —SO—, —CO—, —CHOH—, —NR—C (=NR")—NR'—, R and R' can be hydrogen or alkyl and R" is hydrogen or cyano, or $COY_1$, $Y_1$ is alkoxy radical. Chain B represents an alkyl group —$(CH_2)_n$—, n=0–5 or an alkyl chain of 2–8 carbon atoms interrupted by an oxygen or sulfur atom or a group like —$(CH_2)_n$—O— or —$(CH_2)_n$—S— wherein n=1 or 2. Y represents ($C_1$-$C_8$) alkyl, ($C_3$-$C_6$) cycloalkyl, bicycloalkyl, aryl, cycloalkenyl, heterocycle.

U.S. Pat. No. 5,290,790 discloses compounds of the same general structure as U.S. Pat. No. 4,707,487:

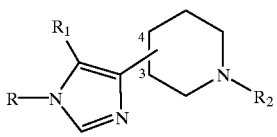

but specifically includes amides wherein $R_2$ is CO—NR'R" and R'R" are independently selected from the group consisting of (a) hydrogen; (b) phenyl or substituted phenyl; (c) alkyl; (d) cycloalkyl; and (e) alkylcycloalkyl such as cyclohexylmethyl or cyclopentylethyl.

SUMMARY OF THE INVENTION

The present invention provides, in its principal aspect, compounds of the general formula:

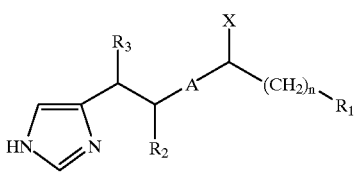

(1.0)

where A is —NHCO—, —N($CH_3$)—CO—, —NHCH$_2$—, —N($CH_3$)—CH$_2$—, —CH=CH—, —COCH$_2$—, —CH$_2$CH$_2$—, —CH(OH)CH$_2$— or —C≡C—;

X is H, $CH_3$, $NH_2$, $NH(CH_3)$, $N(CH_3)_2$, OH, $OCH_3$ or SH;

$R_2$ is hydrogen or a methyl or ethyl group;

$R_3$ is hydrogen or a methyl or ethyl group;

n is 0, 1, 2, 3, 4, 5 or 6; and $R_1$ is selected from the group consisting of (a) alkyl; (b) $C_3$ to $C_8$ cycloalkyl; (c) phenyl or substituted phenyl; (d) heterocyclic; (e) decahydronaphthalene and (f) octahydroindane; or $R_1$ and X may be taken together to denote a 5,6 or 6,6 saturated bicyclic ring structure when X is NH, O, or S.

The pharmaceutically acceptable salts, and individual stereoisomers of compounds of structural formula (1.0) above, as well as mixtures thereof, are also contemplated as falling within the scope of the present invention.

This invention also provides pharmaceutical compositions comprising a pharmaceutically acceptable carrier in combination with an effective amount of a compound of formula (1.0). The present invention also provides a method of treating conditions of therapeutic importance such as allergy, inflammation, cardiovascular disease (i.e. hyper or hypotension), gastrointestinal disorders (acid secretion, motility), cancer, bacterial, viral or fungal disorders as well as CNS disorders involving attention or cognitive disorders, (i.e., Alzheimer's, Attention Deficit Hyperactive Disorder, age-related memory dysfunction, stroke, etc), CNS psychiatric or motor disorders (i.e., depression, schizophrenia, obsessive-compulsive disorders, tourette's syndrome, etc.) and CNS sleep disorders (i.e., narcolepsy, sleep apnea, insomnia, disturbed biological and circadian rhythms, hyper and hyposomnolence, and related sleep disorders), epilepsy, hypothalamic dysfunction (i.e., eating disorders such as obesity, anorexia/bulimia, thermoregulation, hormone release) comprising administering an effective amount of a compound of formula (1.0) to a patient in need of such treatment.

DETAILED DESCRIPTION OF THE INVENTION

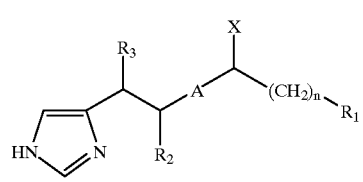

(1.0)

For compounds of formula (1.0), $R_2$ and $R_3$ are H, methyl or ethyl;

A is —NHCO—, —N($CH_3$)—CO—, —NHCH$_2$—, —N($CH_3$)—CH$_2$—, —CH=CH—, —COCH$_2$—, —CH$_2$CH$_2$—, —CH(OH)CH$_2$— or —C≡C—;

X is H, $CH_3$, $NH_2$, $NH(CH_3)$, $N(CH_3)_2$, OH, $OCH_3$, or SH;

$R_2$ is hydrogen or a methyl or ethyl group;

$R_3$ is hydrogen or a methyl or ethyl group;

n is 0, 1, 2, 3, 4, 5 or 6; and $R_1$ is selected from the group consisting of (a) alkyl; (b) $C_3$ to $C_8$ cycloalkyl; (c) phenyl or substituted phenyl; (d) heterocyclic; (e) decahydronaphthalene and (f) octahydroindane; or $R_1$ and X may be taken together to denote a 5,6 or 6,6 saturated bicyclic ring structure when X can be NH, O, or S.

Preferably, the present invention provides compounds of the general formula:

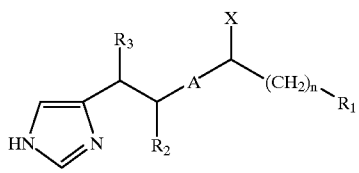

(1.0)

where $R_2$ and $R_3$ are H, methyl or ethyl;
A is —NHCH$_2$—, —N(CH$_3$)—CH$_2$—, —CH=CH—, —COCH$_2$—, —CH$_2$CH$_2$—, —CH(OH)CH$_2$— or —C≡C—;
X is H, CH$_3$, NH$_2$, NH(CH$_3$), N(CH$_3$)$_2$, OH, OCH$_3$ or SH;
$R_2$ is hydrogen or a methyl or ethyl group;
$R_3$ is hydrogen or a methyl or ethyl group;
n is 0, 1, 2, 3, 4, 5 or 6; and
$R_1$ is selected from the group consisting of of (a) alkyl; (b) $C_3$ to $C_8$ cycloalkyl; (c) phenyl or substituted phenyl; (d) heterocyclic; (e) decahydronaphthalene and (f) octahydroindane; or
$R_1$ and X may be taken together to denote a 5,6 or 6,6 saturated bicyclic ring structure when X can be NH, O, or S.

More preferably, the present invention provides compounds of the general formula:

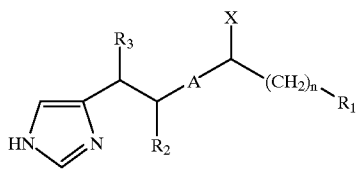

(1.0)

where A is —CH=CH— or —C≡C—;
X is H or NH$_2$;
$R_2$ and $R_3$ are H;
n is 1, 2, 3, 4 or 5; and
$R_1$ is selected from the group consisting of (a) alkyl; (b) $C_3$ to $C_8$ cycloalkyl and (c) phenyl or substituted phenyl; (d) heterocyclic; (e) decahydronaphthalene and (f) octahydroindane.

Most preferably, the present invention provides compounds of the general formula:

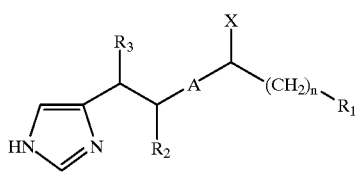

(1.0)

where A is —CH=CH— or —C≡C—;
X is H or NH$_2$;
$R_2$ and $R_3$ are H;
n is 1, 2, 3, 4 or 5;
$R_1$ is selected from the group consisting of (a) alkyl; (b) $C_3$ to $C_8$ cycloalkyl and (c) phenyl or substituted phenyl.

The present invention is also directed to compounds that are useful in the preparation of compounds of formula (1.0). These intermediates are compounds of the formula:

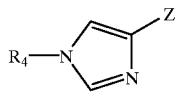

where $R_4$ is —H, triphenylmethyl, 2-(trimethylsilyl)ethoxymethyl (SEM), —SO$_2$N(Me)$_2$, methoxymethyl (MOM), 2-methoxyethoxymethyl (MEM), or other known N-1 imidazole protecting groups; and
Z is (CH$_2$)$_a$B where a is 0, 1, 2, 3 or 4 and B is

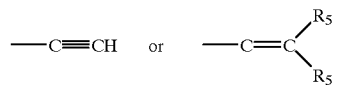

and each $R_5$ can independently be Cl, Br, I or H.

The pharmaceutically acceptable salts, and individual stereoisomers of compounds of structural formula (1.0) above, as well as mixtures thereof, are also contemplated as falling within the scope of the present invention.

Representative compounds of this invention include compounds of the formulae (2.0 through 11.0):

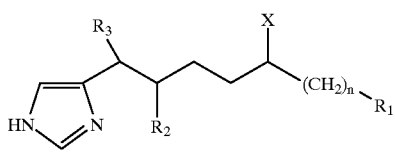

(2.0)

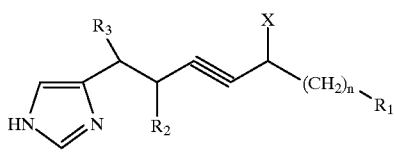

(3.0)

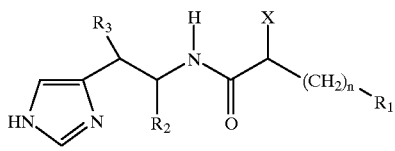

(4.0)

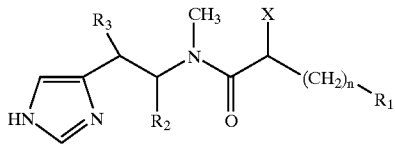

(5.0)

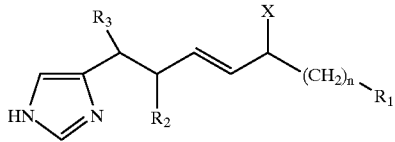

(6.0)

-continued (7.0)

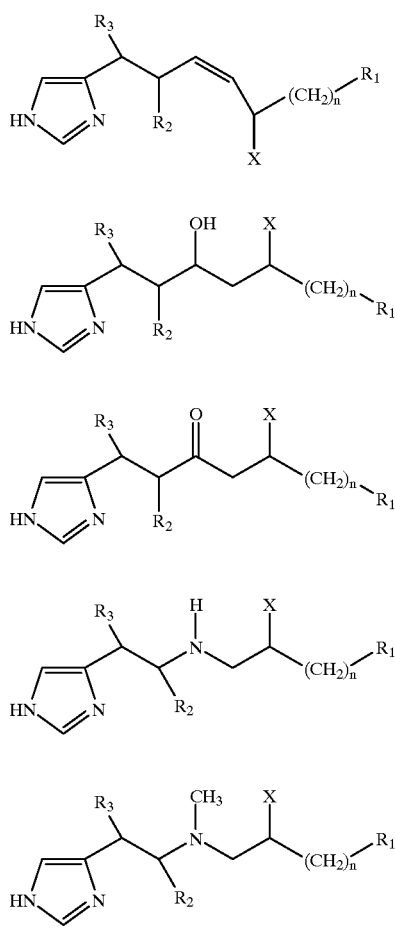

(8.0)

(9.0)

(10.0)

(11.0)

Particulary preferred compounds include:

4-(6-cyclohexylhex-3-ynyl)imidazole (23)

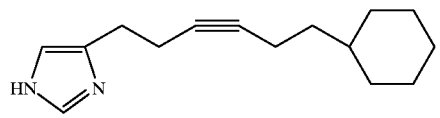

4-(6-cyclohexyhex-cis-3-enyl)imidazole (24)

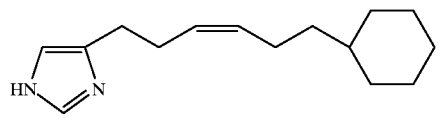

4-(6-cyclohexyhex-trans-3-enyl)imidazole (25)

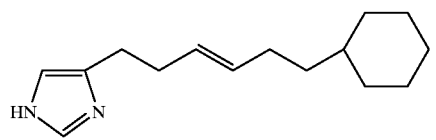

-continued
1-cyclohexyl-6-imidazol-4-ylhex-trans-3-en-2-(S)-ylamine (26)

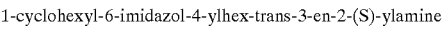

4-(7-methyloct-3-ynyl)imidazole (29)

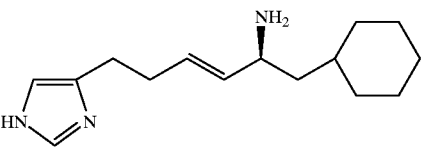

4-(6-cyclopentylhex-3-ynyl)imidazole (30)

4-(8-phenyloct-3-ynyl)imidazole (31)

4-(7,7-dimethyloct-3-ynyl)imidazole (32)

4-non-3-ynylimidazole (33)

4-undec-3-ynylimidazole (34)

4-(7-cyclohexylhept-3-ynyl)imidazole (37)

4-(7-phenylhept-3-ynyl)imidazole (39)

-continued 4-oct-3-ynylimidazole (40)

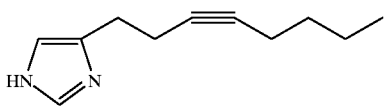

4-(6-phenylhex-cis-3-enyl)imidazole (42)

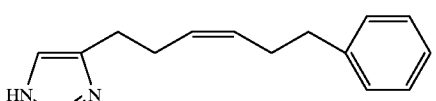

1-cyclohexyl-6-imidazol-4-ylhex-cis-3-en-2-(S)-ylamine

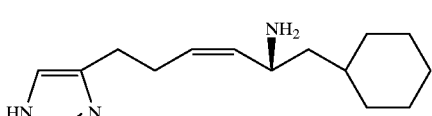

1-cyclohexyl-6-imidazol-4-ylhex-3-yn-2-(S)-ylamine

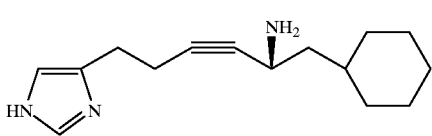

Certain compounds of the invention may exist in different isomeric (e.g., enantiomers and diastereoisomers) forms. The invention contemplates all such isomers both in pure form and in admixture, including racemic mixtures. Enol forms are also included.

The compounds of formula (1.0) can exist in unsolvated as well as solvated forms, including hydrated forms, e.g., hemi-hydrate. In general, the solvated forms, with pharmaceutically acceptable solvents such as water, ethanol, and the like are equivalent to the unsolvated forms for the purposes of the invention.

Certain compounds of the invention also form pharmaceutically acceptable salts, e.g., acid addition salts. For example, the nitrogen atoms may form salts with acids. Examples of suitable acids for salt formation are hydrochloric, sulfuric, phosphoric, acetic, citric, oxalic, malonic, salicylic, malic, fumaric, succinic, ascorbic, maleic, methanesulfonic and other mineral and carboxylic acids well known to those in the art. The salts are prepared by contacting the free base form with a sufficient amount of the desired acid to produce a salt in the conventional manner. The free base forms may be regenerated by treating the salt with a suitable dilute aqueous base solution such as dilute aqueous hydroxide, potassium carbonate, ammonia, and sodium bicarbonate. The free base forms differ from their respective salt forms somewhat in certain physical properties, such as solubility in polar solvents, but the acid salts are equivalent to their respective free base forms for purposes of the invention. (See, for example S. M. Berge, et al., "Pharmaceutical Salts," J. Pharm. Sci., 66: 1–19 (1977) which is incorporated herein by reference.

As throughout this specification and appended claims, the following terms have the meanings ascribed to them:

The term "alkyl" as used herein refers to straight or branched chain radicals derived from saturated hydrocarbons by the removal of one hydrogen atom. These radicals may be unsubstituted or substituted with one or more groups such as halogen, amino, methoxy, or similar groups. Representative examples of alkyl groups include methyl, ethyl, n-propyl, iso-propyl, n-butyl, sec-butyl, iso-butyl, tert-butyl, trifluoromethyl and the like.

The term "heterocyclic" as used herein refers to a closed-ring structure in which one or more of the atoms in the ring is an element other than carbon. Representative groups are preferably saturated and include pyrrolidines, tetrahydrofuranes, tetrahydrothiophenes, tetrahydroisoquinolines and octahydroindole groups.

The term "substituted phenyl" as used herein refers to a phenyl group substituted by one or more groups such as alkyl, halogen, amino, methoxy, and cyano groups.

Individual enantiomeric forms of compounds of the present invention can be separated from mixtures thereof by techniques well known in the art. For example, a mixture of diastereoisomeric salts may be formed by reacting the compounds of the present invention with an optically pure form of the acid, followed by purification of the mixture of diastereoisomers by recrystallization or chromatography and subsequent recovery of the resolved compound from the salt by basification. Alternatively, the optical isomers of the compounds of the present invention can be separated from one another by chromatographic techniques employing separation on an optically active chromatographic medium.

The present invention also provides pharmaceutical compositions which comprise one or more of the compounds of formula (1.0) above formulated together with one or more nontoxic pharmaceutically acceptable carriers. The pharmaceutical compositions may be specifically formulated for oral administration in solid or liquid form, parental injection or for rectal administration.

The pharmaceutical compositions of this invention can be administered to humans and other animals orally, rectally, parenterally, intracisternally, intravaginally, intraperitoneally, topically as by being within the scope of this invention.

Pharmaceutical compositions of this invention for parenteral injection comprise pharmaceutically acceptable sterile aqueous or nonaqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol, and the like), and suitable mixtures thereof, vegetable oils (such as olive oil), and injectable organic esters such as ethyl oleate. Proper fluidity can be maintained, for example, by the use of coating materials such as lecithin, by the maintenance of the required particle size in the case of dispersions, and by the use of surfactants.

These compositions may also contain adjuvants such as preservative, wetting agents and emulsifying agents.

In some cases, in order to prolong the effect of the drug, it is desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions which are compatible with body tissues.

The injectable formulations can be sterilized, for example, by filtration through a bacterial-retaining filter, or by incorporating sterilizing agents in the form of sterile solid compositions which can be dissolved or dispersed in sterile water or other sterile injectable medium just prior to use.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay and i) lubricants such as calcium stearate, magnesium stearate, solid polyethylene glycols, sodium lauryl sulfate and mixtures thereof. In the case of capsules, tablets and pills, the dosage form may also comprise buffering agents.

Solid compositions of a similar type may also be employed as fillers in soft and hardfilled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredients(s) only, or preferentially, in a certain part of the intestinal tract, optionally, in a delayed manner. Examples of embedding compositions which can be used include polymeric substances and waxes.

The active compounds can also be in micro-encapsulated form, if appropriate, with one or more of the above-mentioned excipients.

Liquid dosage forms for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, and perfuming agents.

Suspensions, in addition to the active compounds, may contain suspending agents as, for example, ethoxylated isostearyl alcohols, polyoxyethylene sorbitol and sorbitan esters, microcrystalline cellulose, aluminum methydroxide, bentonite, agar-agar, and tragacanth, and mixtures thereof.

Compositions for rectal or vaginal administration are preferably suppositories which can be prepared by mixing the compounds of this invention with suitable non-irritating excipients or carriers such as cocoa butter, polyethylene glycol or a suppository wax which are solid at room temperature but liquid at body temperature and therefore melt in the rectum or vaginal cavity and release the active compound.

Compounds of the present invention can also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolizable lipid capable of forming liposomes can be used. The present compositions in liposome form can contain, in addition to a compound of the present invention, stabilizers, preservatives, excipients, and the like. The preferred lipids are the phospholipids and the phosphatidyl cholines (lecithins), both natural and synthetic.

Methods to form liposomes are known in the art. See, for example, Prescott, Ed., Methods in Cell Biology, Volume XIV, Academic Press, New York, N.Y. (1976) p. 33 et seq.

Dosage forms for topical administration of a compound of this invention include powders, sprays, ointments and inhalants. The active compound is mixed under sterile conditions with a pharmaceutically acceptable carrier and any needed preservatives, buffers, or propellants which may be required. Opthalmic formulations, eye ointments, powders and solutions are also comtemplated as being within the scope of the invention.

The following processes and techniques may be employed to produce compounds of formula (1.0). The reactions are performed in a solvent appropriate to the reagents and materials employed and suitable for the transformation being effected. It is understood by those skilled in the art of organic synthesis that the functionality present in the molecule must be consistent with the chemical transformation proposed. This will frequently necessitate judgement as to the order of synthetic steps, protecting groups required and deprotection conditions.

A. PREPARATION OF COMPOUNDS WHEREIN A IS —CONH— OR CONCH$_3$—

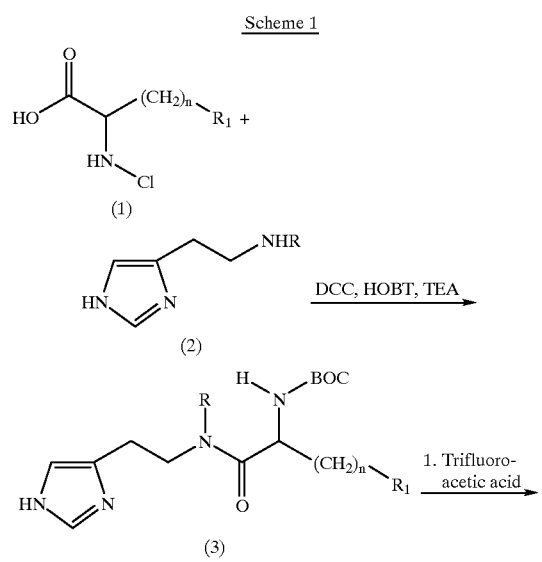

Scheme 1

-continued

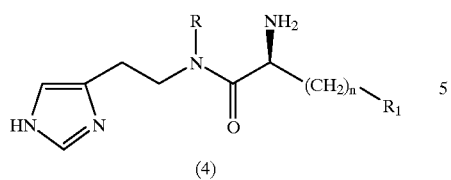

(4)

According to the foregoing reaction scheme I, the N-tert-butoxycarbonyl (BOC), protected amino acid (Natural configuration) 1 is reacted with histamine or N-methyl histamine (2) under standard peptide coupling conditions using 1,3-dicyclohexylcarbodiimide (DCC) and 1-hydroxybenzotriazole (HOBT). After the reaction is complete (tlc or hplc analysis), the amide (3) is treated with trifluoroacetic acid or HCl in dioxane to remove the BOC group and provide the histamine or N-methyl histamine amide (4).

B. PREPARATION OF COMPOUNDS WHEREIN
A IS —NHCH$_2$— OR —N(CH$_3$)CH$_2$—

Scheme II

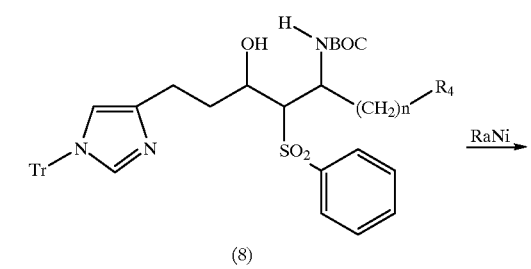

Scheme II

According to the foregoing reaction scheme II, the histamine or N-methylhistaminecarboxamide (4), prepared as described in scheme I, is treated with excess borane-methyl sulfide complex to provide histamine or N-methylhistamine diamine (5).

C. PREPARATION OF COMPOUNDS WHEREIN
A IS —CH(OH)CH$_2$—

Scheme III

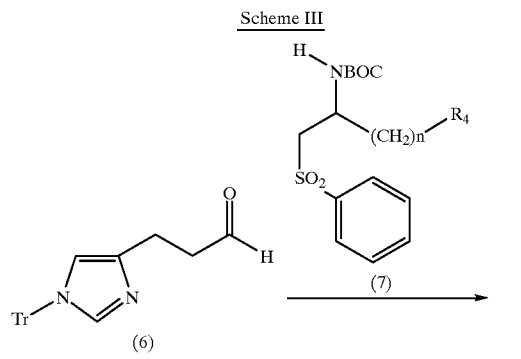

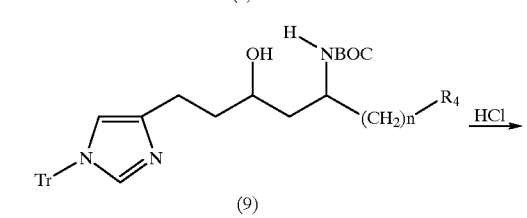

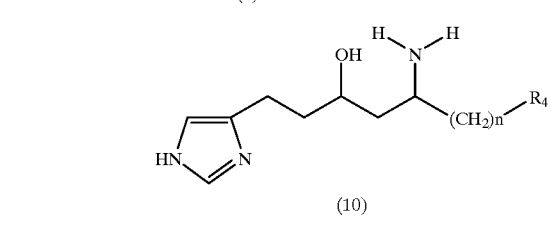

Scheme III

According to the foregoing reaction scheme III, 3-(1-triphenylmethyl-1H-imidazol-4-yl)-propanal (6) is treated with the dianion of sulphone (7), prepared by the reaction of the sulphone with strong base, (n-BuLi) at −78° C. The diastereoisomeric mixture of beta-hydroxy-sulphones (8) produced, is treated with excess Raney nickel (W-2) at room temperature to give a mixture of alcohols (9). The trityl protecting group is removed, as previously described, to provide the [1H-imidazol-4-yl]-amino alcohols (10).

D. PREPARATION OF COMPOUNDS WHEREIN A IS —CH=CH—(trans-olefins)

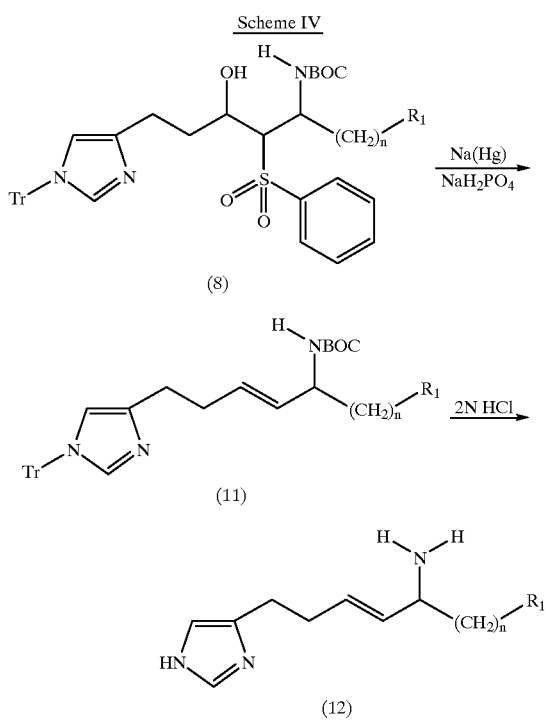

Scheme IV

According to the foregoing reaction scheme IV, the diastereoisomeric mixture of beta-hydroxy sulphones (8) synthesized as described in scheme III, is treated with excess 2–3% Na(Hg) in methanol in the presence of 4 equivalents of sodium hydrogen phosphate buffer to provide the 3-[1-triphenylmethyl-1H-imidazol-4-yl]-trans-olefin (11). Subsequent BOC and trityl deprotection with HCl gives 3-[1H-imidazol-4-yl]-trans-olefin (12).

E. PREPARATION OF COMPOUNDS WHEREIN A IS —C≡C—

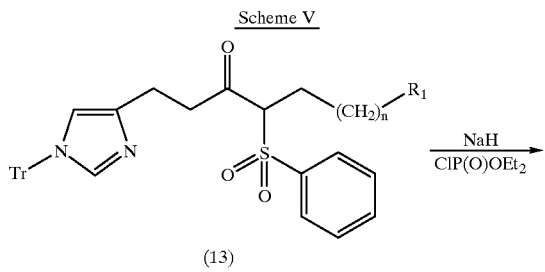

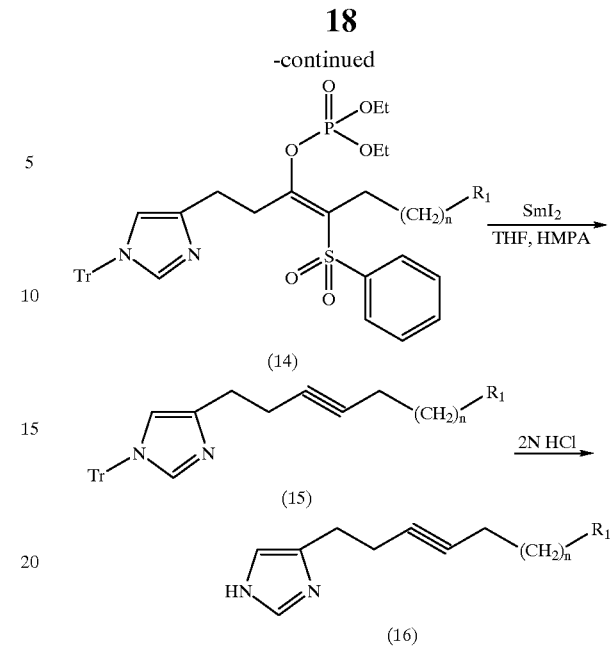

Scheme V

According to the foregoing reaction scheme V, the 3-[1-triphenylmethyl-1H-imidazol-4-yl]-3-keto sulfone (13), is treated with NaH in THF, followed by reaction with diethyl chlorophosphate to give the enol phosphates (14). The enol phosphates are reduced with excess $SmI_2$ in dry THF and 4 mole % hexamethylphosphoramide (HMPA) to provide the 3-[1-triphenylmethyl-1H-imidazol-4-yl]-acetylene (15). Finally, deprotection of the trityl group with HCl gives 3-[1H-imidazol-4-yl]-acetylenes (16).

F. PREPARATION OF COMPOUNDS WHEREIN A IS —CH=CH—(cis-olefins)

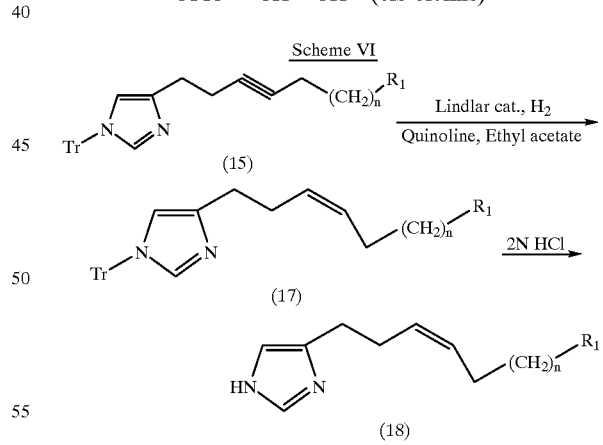

Scheme VI

According to the foregoing reaction scheme VI, 3-[1-triphenylmethyl-1H-imidazol-4-yl]-acetylene (15), prepared as in scheme V is hydrogenated with Lindlar catalyst to afford 3-[1-triphenylmethyl-1H-imidazol-4-yl]-cis-olefin (17). The trityl group is deprotected with HCl to afford 3-[1H-imidazol-4-yl]-cis-olefin (18).

G. PREPARATION OF COMPOUNDS WHEREIN A IS —COCH$_2$—

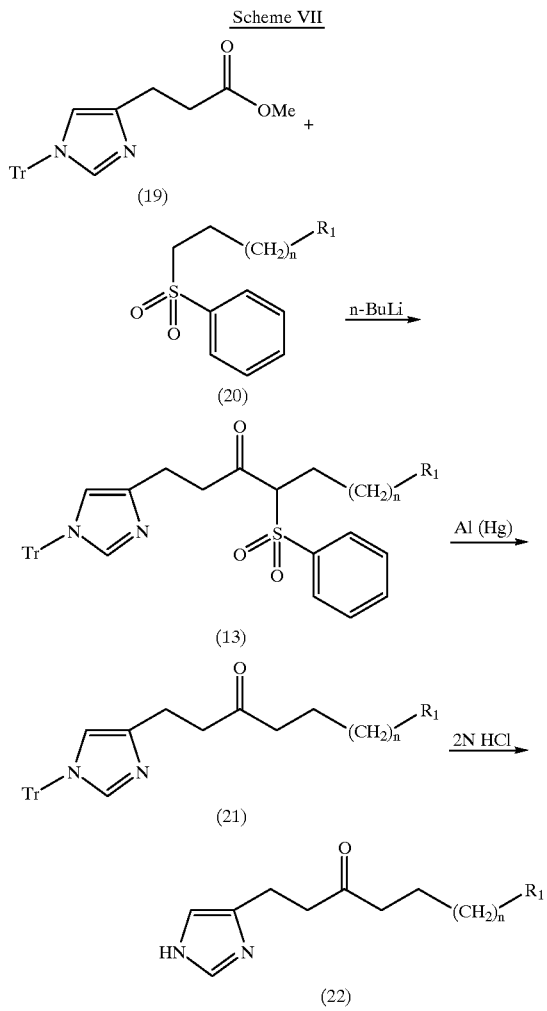

Scheme VII

According to the foregoing reaction scheme VII, condensation of the sulfone anion derived from (20) (treatment with n-BuLi at −78° C., 2.5 equivalents of sulfone: 1 equivalent of methyl ester) with the methyl ester (19) provides 3-[1-triphenylmethyl-1H-imidazol-4-yl]-3-keto sulfone (13). Treatment of ketosulfone (13) with Al(Hg) gives 3-[1-triphenylmethyl-1H-imidazol-4-yl]-ketone (21). Trityl deprotection with HCl gives 3-[1H-imidazol-4-yl]-ketones (22).

H. PREPARATION OF COMPOUNDS WHEREIN A IS —CH$_2$CH$_2$—

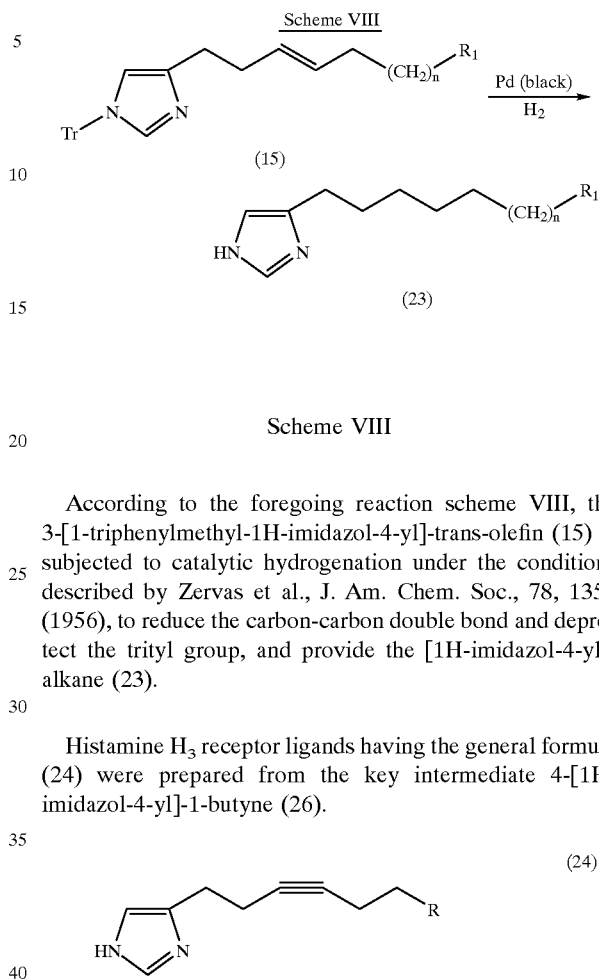

Scheme VIII

According to the foregoing reaction scheme VIII, the 3-[1-triphenylmethyl-1H-imidazol-4-yl]-trans-olefin (15) is subjected to catalytic hydrogenation under the conditions described by Zervas et al., J. Am. Chem. Soc., 78, 1359 (1956), to reduce the carbon-carbon double bond and deprotect the trityl group, and provide the [1H-imidazol-4-yl]-alkane (23).

Histamine H$_3$ receptor ligands having the general formula (24) were prepared from the key intermediate 4-[1H-imidazol-4-yl]-1-butyne (26).

This intermediate (26) is available from aldehyde (6) following either of two synthetic pathways outlined in scheme IX. Preparation of the vinyl dibromide (25) by the standard treatment with triphenylphosphine and carbon tetrabromide is quite tedious due to problems of triphenylphosphine oxide separation. The three step preparation of (25) from (6) gave comparable overall yields (70%). Treatment of vinyl dibromide (25) with an excess of n-BuLi gave the terminal acetylene (26) (90%). The acetylenes were obtained by alkylation of (26) followed by deprotection of the trityl group as shown in scheme X.

Scheme IX

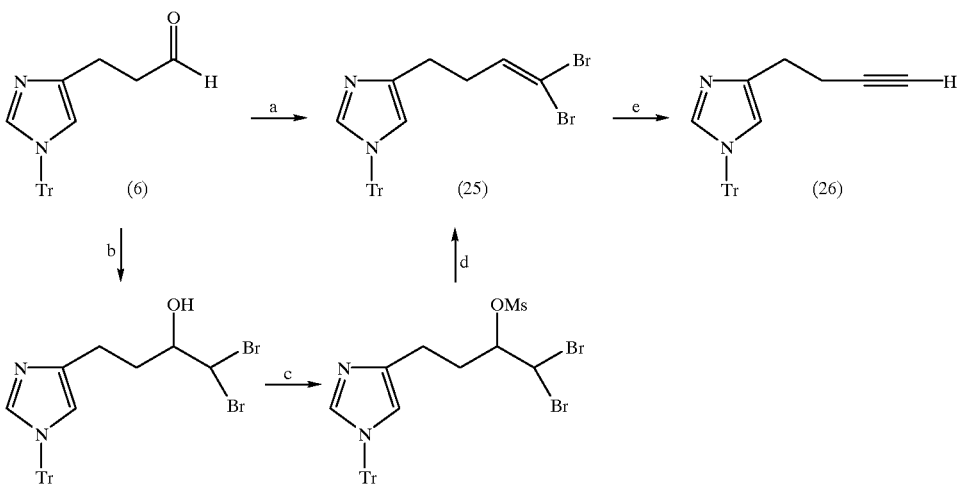

Reagents (a) PPh₃, CBr₄; (b) Dibromomethane, Lithium dicyclohexylamide, -78° C., THF; (c) MsCl, TEA, THF, 0° C.; (d) TEA, THF, room temperature; (e) 2 equiv. n-BuLi, THF, -78° C.

Alkylation of the terminal acetylene (26) were obtained with reactions performed using n-BuLi:N,N,N¹,N¹-tetramethylethylenediamine (TMEDA) complex in tetrahydrofuran at 55° C. for 24–36 hours (Scheme X).

Scheme X

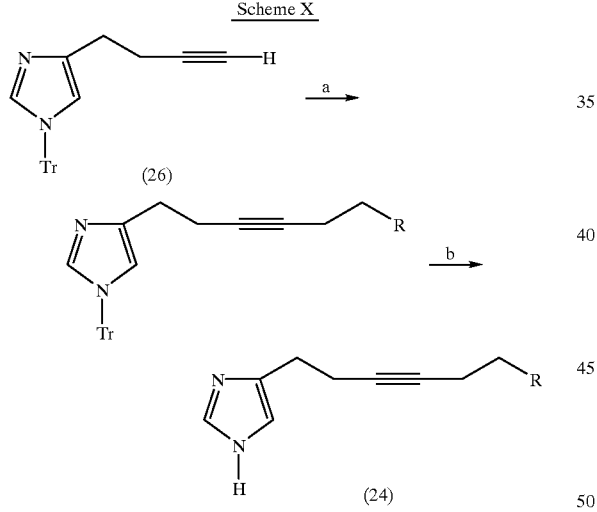

Reagents: (a) n-BuLi:TMEDA, R—I, 55° C., 24 hr; (b) 1N HCl, EtOH, 90° C., 1hr

The present invention is further illustrated by the following representative examples:

EXAMPLE 1

Preparation of (L)-phenylalanine-histamine amide (2-(S)-amino-N-(2-imidazol-4-yletyl)-3-phenyl propanamide)

n-BOC-(L)-phenylalanine (1.32 g, 5 mmol) was dissolved in dry THF (30 ml) and cooled to 0° C. under N₂. N-Methyl morpholine (0.66 ml, 6 mmol) was added, followed by the dropwise addition of isobutylchloroformate (0.65 ml, 5 mmol). After 10 min at 0° C., histamine dihydrochloride (1.11 g, 6 mmol) and triethylamine (1.68 ml, 12 mmol) in THF/H₂O (2 ml) was added and the reaction mixture stirred for 2 hours. 5% NaHCO₃ solution was added, and the mixture was partioned between ethyl acetate and water (50 ml/50 ml). The ethyl acetate layer was separated, washed with 5% NaHCO₃ solution, separated, dried over MgSO₄, filtered and evaporated in vacuo to obtain the crude amino N-BOC protected (L)-phenylalanine-histamine amide. The BOC group was removed directly by treatment with trifluoroacetic acid (10 ml) for 30 min. TFA was evaporated and the residue triturated with ether and the ditrifluoroacetic salt of (L)-phenylalanine-histamine amide (1.20 g) collected by filtration. Samples for the H₃ receptor binding assay was further purified by reverse phase HPLC.

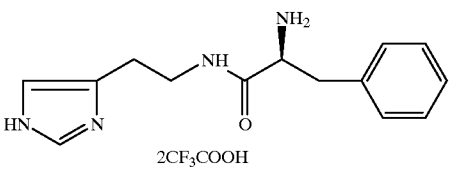

Di-trifluoroacetic acid salt 2-(S)-Amino-N-(2-imidazol-4-yletyl)-3-phenyl propanamide (1) ¹H-NMR (300 MHz, D₂O): δ8.44 (s, 1H), 7.2 (m, 3H), 7.10 (m, 2H), 6.90 (s, 1H), 4.02 (AB q, 1H), 3.43 (m, 1H), 3.22 (m, 1H), 3.04 (dd, 1H), 2.94 (dd, 1H), 2.64 (m, 2H); Mass Spectrum (+FAB): [259 (M+1)⁺, 100%] MW=258.3249, C₁₄H₁₈N₄O.

EXAMPLE 2

Preparation of (L)-proline-histamine amide (N-(2-imidazol-4-ylethyl)-(S)-pyrrolidin-2-ylformamide)

(L)-Proline-histamine amide was prepared as example 1 except (L)-proline was used instead of (L)-phenylalanine.

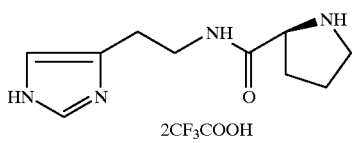

2CF₃COOH

Di-trifluoroacetic acid salt
N-(2-Imidazol-4-ylethyl)-(S)-pyrrolidin-2-ylformamide (2) ¹H—NMR (300 MHz, D₂O): δ8.44 (s, 1H), 7.16 (s, 1H), 4.20 (AB q, 1H), 3.52 (m, 1H), 3.42 (m, 1H), 3.28 (m, 2H), 2.87 (m, 2H), 2.28 (m, 1H), 1.9 (m, 3H); Mass Spectrum (+FAB): [209 (M+1)⁺, 100%] MW=208.2649, C₁₀H₁₆N₄O.

EXAMPLE 3

Preparation of (L)-L-1,2,3,4-tetrahydroisoguinoline-3-carboxylic acid (TIC)-histamine amide (N-2-imidazol-4-ylethyl)-(S)-3-1,2,3,4-tetrahydroisoquinolylformamide)

(L)-Tic-histamine amide was prepared as example 1 except (L)-TIC was used.

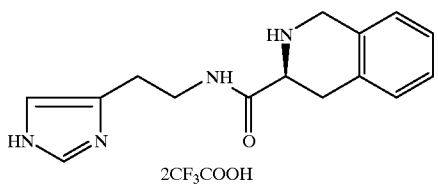

2CF₃COOH

Di-trifluoroacetic acid salt
N-2-Imidazol-4-ylethyl)-(S)-3-1,2,3,4-tetrahydroisoquinolyltormamide (3) ¹H—NMR (300 MHz, D₂O): δ8.46 (s, 1H), 7.24 (m, 2H), 7.15 (m, 2H), 7.09 (s, 1H), 4.33 (AB q, 2H), 4.22 (m, 1H), 3.60 (m, 1H), 3.40 (m, 1H), 3.20 (dd, 1H), 3.02 (dd, 1H), 2.86 (m, 2H); Mass Spectrum (+FAB): [271 (M+1)⁺, 100%] MW=270.3359, C₁₅H₁₈N₄O.

EXAMPLE 4

Preparation of (D)-phenylalanine-histamine amide (2-(R)-amino-N-(2-imidazol-4-yletyl)-3-phenyl propanamide)

Phenylalanine-histamine amide was prepared in the same manner as example 1 except (D)-phenylalanine was used.

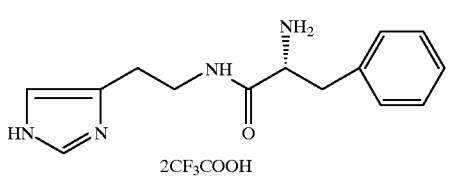

2CF₃COOH

Di-trifluoroacetic acid salt (D-isomer)
2-(R)-Amino-N-(2-imidazol-4-yletyl)-3-phenyl propanamide (4) ¹H-NMR (300 MHz, D₂O): δ8.44 (s, 1H), 7.20 (m, 3H), 7.10 (m, 2H), 6.90 (s, 1H), 4.02 (AB q, 1H), 3.43 (m, 1H), 3.22 (m, 1H), 3.04 (dd, 1H), 2.94 (dd, 1H), 2.64 (m, 2H); Mass Spectrum (+FAB): [259 (M+1)⁺, 100%] MW=258.3249, C₁₄H₁₈N₄O.

EXAMPLE 5

Preparation of (L)-p-fluorophenylalanine-histamine amide (2-(S)-amino-3-(4-flurophenyl)-N-(2-imidazoyl-4-ylethyl)propanamide).

(L)-p-Fluorophenylalanine-histamine amide was prepared in the same manner as example 1, except (L)-p-fluorophenylalanine was used.

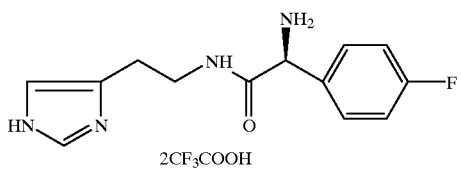

2CF₃COOH

Di-trifluoroacetic acid salt
2-(S)-Amino-3-(4-flurophenyl)-N-(2-imidazoyl-4-ylethyl) propanamide (5) ¹H-NMR (300 MHz, D₂O): δ8.46 (s, 1H), 7.09 (m, 2H), 6.95 (m, 3H), 4.00 (dd, 1H), 3.46 (m, 1H), 3.26 (m, 1H), 3.06 (dd, 1H), 2.94 (dd, 1 H), 2.68; Mass Spectrum (+FAB): [277 (M+1)⁺, 100%] MW=276.3153, C₁₄H₁₇N₄O₁F₁.

EXAMPLE 6

Preparation of (L)-cyclohexylalanine-histamine amide (2-(S)-amino-3-cyclohexyl-N-(2-imidazol-4-ylethyl)propanamide)

(L)-Cyclohexylalanine-histamine amide was prepared in the same manner as example 1, except (L)-cyclohexylalanine was used.

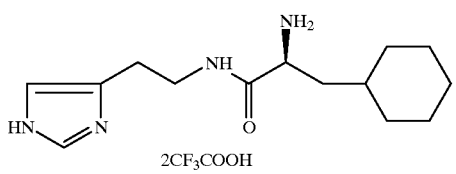

2CF₃COOH

Di-trifluoroacetic acid salt
2-(S)-Amino-3-cyclohexyl-N-(2-imidazol-4-ylethyl) propanamide (6) ¹H-NMR (300 MHz, D₂O): δ8.56 (s, 1H), 7.20 (s, 1H), 3.82 (m, 1H), 3.65 (m, 1H), 3.45 (m, 1H), 3.34 (m, 1H), 2.88 (m, 2H), 1.5 (m, 6H), 1.0 (m, 4H), 0.80 (m, 1H); Mass Spectrum (+FAB): [265 (M+1)⁺, 100%] MW=264.3729, C₁₄H₂₄N₄O₁.

EXAMPLE 7

Preparation of (L)-N-methylphenylalanine-histamine amide (N-(2-imidazol)-4-ylethyl-2-(S)-(methylamino)-3-phenylpropanamide)

(L)-N-Methylphenylalanine-histamine amide was prepared in the same manner as example 1, except (L)-N-methylphenylalanine was used.

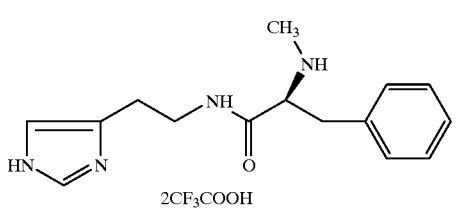

Di-trifluoroacetic acid salt
N-(2-Imidazol)-4-ylethyl)-2-(S)-(methylamino)-3-phenylpropanamide (7) $^1$H-NMR (300 MHz, D$_2$O): δ8.44 (s, 1H), 7.20 (m, 3H), 7.10 (m, 2H), 6.86 (s, 1H), 3.92 (m, 1H), 3.42 (m, 1H), 3.20 (m, 2H), 2.94 (dd, 1H), 2.62 (m, 2H), 2.57 (s, 3H); Mass Spectrum (+FAB): [273 (M+1)$^+$, 100%] MW=272.3519, C$_{15}$H$_{20}$N$_4$O$_1$.

EXAMPLE 8

Preparation of (L)-3-(2'-naphthyl)-alanine-histamine amide (2-(S)-amino-N-(2-imidazol-4-ylethyl)-3-naphthylpropanamide)

(L)-3-(2'-Naphthyl)-alanine-histamine amide was prepared in the same manner as example 1 except (L)-3-(2'-naphthyl)-alanine was used.

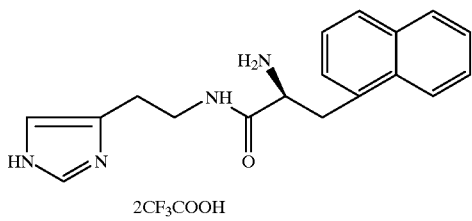

Di-trifluoroacetic acid salt
2-(S)-Amino-N-(2-imidazol-4-ylethyl)-3-naphthylpropanamide (8) $^1$H-NMR (300 MHz, D$_2$O): δ8.4 (s, 1H), 7.91 (d, 1H), 7.82 (d, 1H), 7.72 (d, 1H), 7.5 (m, 2H), 7.33 (m, 2H), 6.5 (s, 1H), 4.16 (m, 1H), 3.5 (m, 2H), 3.22 (m, 1H), 2.96 (m, 1H), 2.24 (m, 2H); Mass Spectrum (+FAB): [309 (M+1)$^+$, 100%] MW=308.3849, C$_{18}$H$_{20}$N$_4$O$_1$.

EXAMPLE 9

Preparation of (L)-2-phenylglycine-histamine amide (2-(S)-amino-N-(2-imidazol-4-ylethyl)-2-phenylethanamide)

(L)-2-Phenylglycine-histamine amide was prepared in the same manner as example 1 except (L)-2-phenylglycine was used.

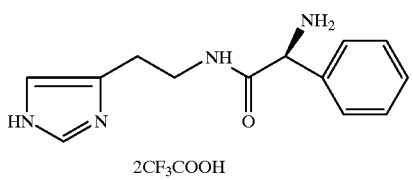

Di-trifluoroacetic acid salt
2-(S)-Amino-N-(2-imidazol-4-ylethyl)-2-phenylethanamide (9) $^1$H NMR (300 MHz, D$_2$O): δ8.38 (s, 1H), 7.41 (m, 3H), 7.24 (m, 2H), 6.6 (s, 1H), 3.7 (m, 1H), 3.25 (m, 1H), 3.19 (m, 1H), 2.8 (m, 1H), 2.7 (m, 1H); Mass Spectrum (+FAB): [245 (M+1)$^+$, 100%] MW=244.2979, C$_{13}$H$_{16}$N$_4$O$_1$.

EXAMPLE 10

Preparation of (L)-N-acetylphenylalanine-histamine amide (2-(S)-(acetylamino)-3-cyclohexyl-N-(2-imidazol-4-ylethyl)propanamide)

(L)-N-Acetylphenylalanine-histamine amide was prepared in the same manner as example 1 except (L)-N-acetylphenylalanine was used and no BOC deprotection step was necessary.

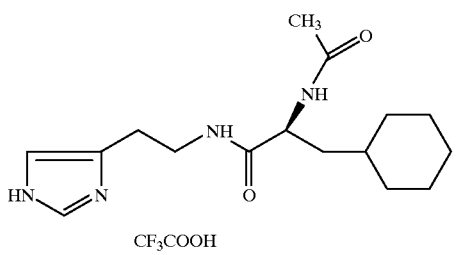

Trifluoroacetic acid salt
2-(S)-(Acetylamino)-3-cyclohexyl-N-(2-imidazol-4-yethyl) propanamide (10) $^1$H-NMR (300 MHz, D$_2$O): δ8.49 (s, 1H), 7.17 (s, 1H), 4.06 (dd, 1H), 3.40 (m, 2H), 2.83 (t, 2H), 1.90 (s, 3H), 1.52 (m, 6H), 1.36 (m, 1H), 1.04 (m, 4H), 0.78 (m, 2H); Mass Spectrum (+FAB): [307 (M+1)$^+$, 100%] MW=306.4109, C$_{16}$H$_{26}$N$_4$O$_2$.

EXAMPLE 11

Preparation of (L )-homophenylalanine-histamine amide (2-(S)-amino-N-(2-imidazol-4-ylethyl)-4-phenylbutanamide)

(L)-Homophenylalanine-histamine amide was prepared in the same manner as example 1 except (L)-homophenylalanine was used.

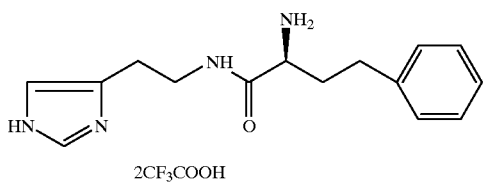

Di-trifluoroacetic acid salt
2-(S)-Amino-N-(2-imidazol-4-ylethyl)-4-phenylbutanamide (11) $^1$H-NMR (300 MHz, D$_2$O): δ8.42 (s, 1H), 7.19 (m, 6H), 3.85 (m, 1H), 3.52 (m, 1H), 3.35 (m, 1H), 2.82 (m, 2H), 2.46 (m, 2H), 2.00 (m, 2H); Mass Spectrum (+FAB): [273 (M+1)$^+$, 100%] MW=272.3518, C$_{15}$H$_{20}$N$_4$O$_1$.

EXAMPLE 12

Preparation of (L )-L-octahydroindole-2-carboxylic acid (OIC)-histamine amide ((7-azabicyclo[4.3.0] non-(S)-8-yl)-N-(2-imidazol-4-ylethyl)formamide)

(L)-OIC-histamine amide was prepared in the same manner as example 1 except (L)OIC was used.

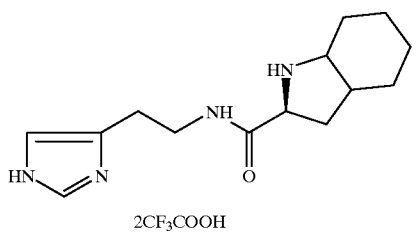

Di-trifluoroacetic acid salt
(7-Azabicyclo[4.3.0]non-(S)-8-yl)-N-(2-imidazol-4-ylethyl)formamide (12) ¹H-NMR (300 MHz, D₂O): δ8.54 (s, 1H), 7.18 (s, 1H), 4.26 (m, 1H), 3.65 (m, 2H), 3.4 (m, 1H), 2.87 (m, 2H), 2.32 (m, 2H), 1.92 (m, 1H), 1.75 (m, 2H), 1.58–1.20 (m, 6H); Mass Spectrum (+FAB): [263 (M+1)⁺, 100%] MW=262.3569, $C_{14}H_{22}N_4O_1$.

EXAMPLE 13

Preparation of O-benzyl-(L)-tyrosine-histamine amide (2-(S)-amino-N-(2-imidazol-4-ylethyl)-3-(4-(phenylmethoxy)phenyl)propanamide)

O-Benzyl-(L)-tyrosine-histamine amide was prepared in the same manner as example 1 except N-BOC-O-benzyl-(L)-tyrosine was used.

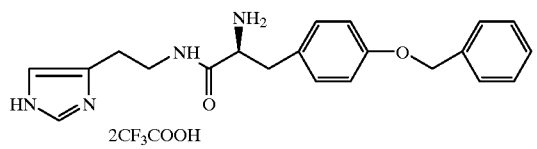

Di-trifluoroacetic acid salt
2-(S)-Amino-N-(2-imidazol-4-ylethyl)-3-(4-(phenylmethoxy)phenyl) propanamide (13) ¹H-NMR (300 MHz, D₂O): δ8.42 (s, 1H), 7.3 (m, 5H), 7.02 (d, 2H), 6.86 (m, 3H), 5.1 (s, 2H), 3.97 (dd, 1H), 3.44 (m, 2H), 3.18 (m, 1H), 3.02 (dd, 1H), 2.90 (m, 1H), 2.55 (m, 1H); Mass Spectrum (+FAB): [365 (M+1)⁺, 100%] MW=364.4499, $C_{21}H_{24}N_4O_2$.

EXAMPLE 14

Preparation of O-benzyl-(L)-serine-histamine amide (2-(S)-amino-N-(2-imidazol-4-ylethyl)-3-(phenylmethoxy)propanamide)

O-benzyl-(L)-serine-histamine amide was prepared in the same manner as example 1, except N-BOC-O-benzyl-(L)-serine was used.

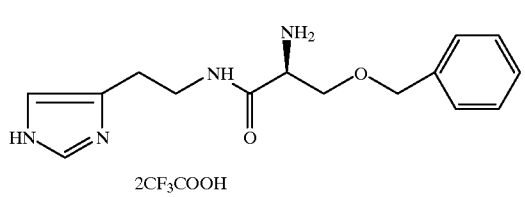

Di-trifluoroacetic acid salt
2-(S)-Amino-N-(2-imidazol-4-ylethyl)-3-(phenylmethoxy) propanamide (14) ¹H-NMR (300 MHz, D₂O): δ8.38 (s, 1H), 7.32 (m, 3H), 7.25 (m, 2H), 7.05 (s,1H), 4.45 (AB q, 2H), 4.07 (m, 1H), 3.7 (m, 2H), 3.48 (m, 1H), 3.37 (m, 1H), 2.8 (m, 2H); Mass Spectrum (+FAB): [289 (M+1)⁺, 100%] MW=288.3518, $C_{15}H_{20}N_4O_2$.

EXAMPLE 15

Preparation of (L)-aspartic acid B-benzyl ester-histamine amide(phenylmethyl-3-(S)-amino-3-(N-(2-imidazol-4-ylethyl)carbamoyl) propanoate)

(L)-Aspartic acid B-benzyl ester-histamine amide was prepared in the same manner as example 1, except N-BOC-(L)-aspartic acid B-benzyl ester was used.

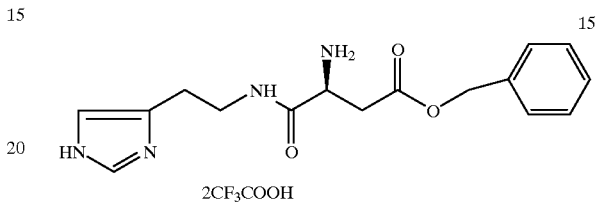

Di-trifluoroacetic acid salt
Phenylmethyl-3-(S)-amino-3-(N-(2-imidazol-4-ylethyl) carbamoyl) propanoate (15) ¹H-NMR (300 MHz, D₂O): δ8.40 (s, 1H), 7.35 (m, 5H), 7.05 (s, 1H), 5.10 (s, 2H), 4.19 (m, 1H), 3.4 (m, 1H), 3.3 (m, 1H), 2.94 (m, 2H), 2.7 (m, 2H); Mass Spectrum (+FAB): [317 (M+1)⁺, 100%] MW=316.3629, $C_{16}H_{20}N_4O_3$.

EXAMPLE 16

Preparation of (L)-histidine-histamine amide (2-(S)-amino-3-imidazol-4-yl-N-(2-imidazol-4-ylethyl) propanamide)

(L)-Histidine-histamine amide was prepared in the same manner as example 1 except N-BOC-(L)-histidine was used.

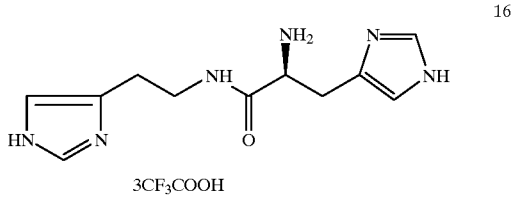

Tri-trifluoroacetic acid salt
2-(S)-Amino-3-imidazol-4-yl-N-(2-imidazol-4-ylethyl) propanamide (16) ¹H-NMR (300 MHz, D₂O): δ8.54 (s, 1H), 8.50(s, 1H), 7.28 (s, 1H), 7.14 (s,1H), 4.11 (m, 1H), 3.43 (m, 4H), 3.22 (d, 2H), 2.80 (m, 4H). Mass Spectrum (+FAB): [249 (M+1)⁺, 100%] MW=248.2894, $C_{11}H_{16}N_6O_1$.

EXAMPLE 17

Preparation of N-PMC-(L)-arginine-histamine amide (2-(S)-amino-N-(2-imidazol-4yiethyl)-5-((imino(((2,2,5,7,8-pentamethylchroman-6-yl)sulfonyl)amino)methyl)amino)pentanamide)

N-α-FMOC-N-PMC-(L)-arginine (0.66 g, 1 mmol) was dissolved in 20 ml of dry THF and cooled to 0° C. under N₂. N-Methyl morpholine (0.11 ml, 1 mmol) was added, followed by isobutylchloroformate (0.13 ml, 1 mmol). After 10 min, histamine dihydrochloride (0.37 g, 2 mmol) and triethylamine (0.56 ml, 4 mmol) in 2 ml of water was added. After 1 hour the reaction mixture was partioned between ethyl acetate and water (50 ml/50 ml), and washed with 5% NaHCO$_3$. The ethyl acetate layer was separated, dried over MgSO$_4$, filtered, and evaporated to provide crude N-α-FMOC-N-PMC-(L)-arginine-histamine amide. The FMOC group was cleaved by treatment with DEA in THF (10 ml) for 4 hours. The reaction mixture was evaporated to dryness, the solid filtered and washed with ether (3×50 ml) to give N-PMC-(L)-arginine-histamine amide (500 mg). A sample for in vitro testing was further purified by reverse phase HPLC.

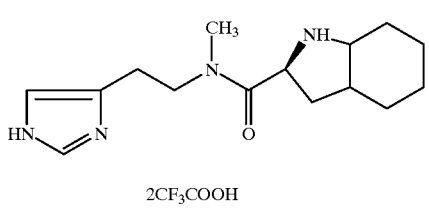

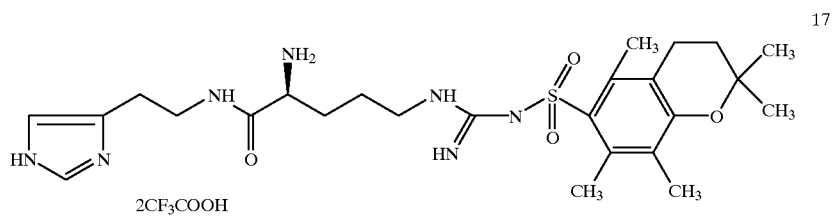

Di-trifluoroacetic acid salt 2-(S)-Amino-N-(2-imidazol-4ylethyl)-5-((imino(((2,2,5,7,8-pentamethylchroman-6-yl)sulfonyl)amino)methyl)amino) pentanamide (17) $^1$H-NMR (300 MHz, D$_2$O): δ8.5 (s, 1H), 7.04 (s, 1H), 3.81 (m, 1H), 3.5 (m, 1H), 3.35 (m, 1H), 3.09 (m, 2H), 2.8 (m, 2H), 2.57 (m, 2H), 2.42 (s, 3H), 2.39 (s, 3H), 2.00 (s, 3H), 1.73 (m, 2H), 1.67 (m, 2H), 1.37 (m, 2H); Mass Spectrum (+FAB): [534 (M+1)$^+$, 100%] MW=533.7001, C$_{25}$H$_{39}$N$_7$O$_4$S$_1$.

EXAMPLE 18

Preparation of (L)-OIC-N-methylhistamine amide ((7-azabicyclo[4.3.0]non-(S)-8-yl)-N-(2-imidazol-4-ylethyl)-N-methylformamide)

N-Methylhistamine dihydrochloride (100 mg, 0.5 mmol) dissolved in THF/DMSO (4:1 ml) and a few drops of water was neutralized with triethylamine (0.14 ml, 1 mmol). To a solution of N-BOC-(L)-OIC. (0.27 g, 1 mmol) dissolved in THF (5 ml) was added HOBT (0.30 g, 2 mmol) followed by the addition of DIC (0.126 g, 1 mmol). After 10 min, this mixture was added with stirring to the solution of N-methylhistamine and the reaction was stirred overnight. The mixture was diluted with ethyl acetate/water (50 ml). The organic layer was separated, washed with 5% NaHCO$_3$, saturated NaCl solution, dried over MgSO$_4$ and evaporated to dryness. The crude N-BOC-(L)-OIC-N-methylhistamine amide was deprotected by treatment with trifluoroacetic acid (10 ml) for 45 min. The TFA was evaporated and the residue repeatedly washed with methanol. Purification of the crude residue by reverse phase HPLC and freeze drying gave 100 mg of (L)-OIC-N-methylhistamine amide ditrifluoroacetic acid salt.

Di-trifluoroacetic acid salt
(7-Azabicyclo[4.3.0]non-(S)-8-yl)-N-(2-imidazol-4-ylethyl)-N-methylformamide (18) $^1$H-NMR (300 MHz, D$_2$O): δ8.58 (s, 1H), 7.22 (s, 1H), 4.58 (m, 1H), 3.98 (m, 1H), 3.70 (m, 1H), 3.26 (m, 1H), 2.95 (s, 3H), 2.94 (m, 2H), 2.5 (m, 1H), 2.30 (m, 1H), 1.86-1.00 (m, 9H). Mass Spectrum (+FAB): [277 (M+1)$^+$, 100%] MW=276.3839, C$_{15}$H$_{24}$N$_4$O$_1$.

EXAMPLE 19

Preparation of (L)-arginine-histamine amide (5-(amidinoamino)-2-(S)-amino-N-(2-imidazol-4-ylethyl)pentanamide)

N-PMC-(L)-arginine-histamine amide (150 mg), prepared as in example 17 was treated with trifluoroacetic acid-phenol (9:1) solution (5 ml) for 2 hours. Trifluoroacetic acid was evaporated and the residue triturated with ether (3×50 ml). The ether was decanted, and the residue dissolved in water and purified by HPLC to afford 90 mgs of (L)-arginine-histamine amide.

Tri-trifluoroacetic acid salt
5-(Amidinoamino)-2-(S)-amino-N-(2-imidazol-4-ylethyl) pentanamide (19) $^1$H-NMR (300 MHz, D$_2$O): δ8.50 (s, 1H), 7.19 (s, 1H), 3.48 (m, 2H), 3.09 (m, 2H), 2.87 (m, 2H), 1.75 (m, 2H), 1.45 (m, 2H). Mass Spectrum (+FAB): [268 (M+1)$^+$, 100%] MW=267.3361, C$_{11}$H$_{21}$N$_7$O$_1$.

EXAMPLE 20

Preparation of (L)-leucine-histamine amide (2-(S)-amino-N-(2-imidazol-4-ylethyl)-4-methylpentanamide)

(L)-Leucine-histamine amide was prepared in the same manner as example 1 except N-BOC-(L)-leucine was used.

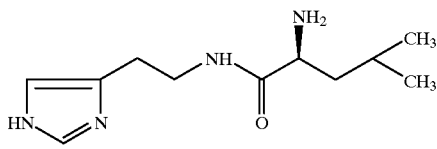

2CF₃COOH

Di-trifluoroacetic acid salt
2-(S)-Amino-N-(2-imidazol-4-ylethyl)-4-methylpentanamide (20) ¹H-NMR (300 MHz, D₂O): δ8.5 (s, 1H), 7.2 (s, 1H), 3.78 (m, 1H), 3.65 (m, 1H), 3.35 (m, 1H), 2.88 (m, 2H), 1.50 (m, 2H), 1.26 (m, 1H), 0.79 (d, 6H); Mass Spectrum: (+FAB): [225 (M+1)⁺, 100 %] MW=224.3079, $C_{11}H_{20}N_4O_1$.

EXAMPLE 21

Preparation of -(L)-OIC-α-methy-histamine amide ((7-azabicyclo[4.3.0]non-(S)-8-yl-N-(2-imidazol-4-yl-(R)-methylethyl)formamide)

N-BOC-(L)-OIC (0.269 g, 1 mmol), HOBT (0.150 g, 1 mmol) and DIC (0.126 g, 1 mmol) was dissolved in THF (5 ml). After 10 min, the N-BOC-(L)-OIC HOBT ester was added to a solution of α-methylhistamine dihydrochloride (0.100 g, 0.5 mmol) and triethylamine (0.14 ml, 1 mmol) in isopropanol (5 ml). The reaction mixture was stirred for 18 hours at room temperature and then partioned between ethyl acetate and water (50 ml). The ethyl acetate layer was separated, washed with 5% NaHCO₃, water and dried over MgSO₄. After evaporation in vacuo, the BOC group was removed by treatment with trifluoroacetic acid (5 ml) for 30 min, and the crude product purified by HPLC chromatography to afford 70 mgs of-(L)-OIC-α-methyhistamine amide.

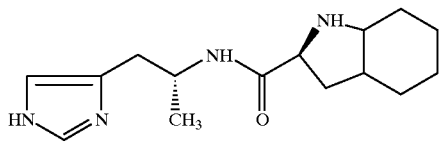

2CF₃COOH

Di-trifluoroacetic acid salt
(7-Azabicyclo[4.3.0]non-(S)-8-yl-N-(2-imidazol-4-yl-(R)-methylethyl)formamide (21) ¹H-NMR (300 MHz, D₂O): δ8.51 (s, 1H), 7.2 (s, 1H), 4.24 (m, 1H), 4.11 (m, 1H), 3.72 (m, 1H), 2.86 (m, 2H), 2.36 (m, 2H), 2.18-1.22 (m, 9H), 1.14 (d, 3H); Mass Spectrum (+FAB): [277 (M+1)⁺, 100%] MW=276.3839, $C_{15}H_{24}N_4O_1$.

EXAMPLE 22
Preparation of reduced -(L)-OIC-histamine amide (((7-azabicyclo[4.3.0]non-(S)-8-yl)methyl)(2-imidazol-4-ylethyl)amine)

N-BOC-(L)-OIC-histamine amide (0.140 g, 0.396 mmol) prepared as in example 12, was dissolved in dry THF (10 ml) and heated to 60° C. under N₂. BH₃(SMe₂) (0.237 ml, 6 equiv.) was added dropwise to the solution and the reaction stirred for 30 min. The reaction was cooled to room temperature, TMEDA (0.068 g) was added, the reaction mixture stirred for additional 1 hour, and then the organic volatiles removed with a rotary evaporator. To the crude residue was added trifluoroacetic acid (5 ml), and the reaction was stirred for 30 min. TFA was evaporated and the crude product was purified by reverse phase HPLC. to give 40 mgs of the reduced (L)-OIC-histamine amide.

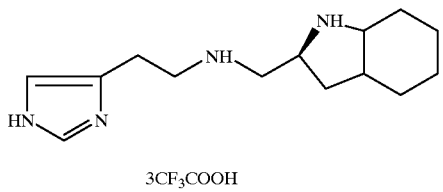

3CF₃COOH

Tri-trifluoroacetic acid salt
((7-Azabicyclo[4.3.0]non-(S)-8-yl)methyl)(2-imidazol-4-ylethyl)amine (22) ¹H-NMR (300 MHz, D₂O): δ8.54 (s, 1H), 7.18 (s, 1H), 4.06 (m, 1H), 3.45 (m, 2H), 3.4 (m, 1H), 3.35 (m,2H), 2.87 (m, 2H), 2.32 (m, 2H), 1.92 (m, 1H), 1.75 (m, 2H), 1.58-1.20 (m, 6H); Mass Spectrum (+FAB): [249 (M+1)⁺, 100%] MW=248.3729, $C_{14}H_{24}N_4$.

EXAMPLE 23

Preparation of 1-[1H-imidazol-4-yl]-6-cyclohexyl-3-hexyne (4-(6-cycloheylhex-3-ynyl)imidazole)

Step 1

3-cyclohexylpropyl-p-toluene sulfone (32.2 g, 0.115 mol) was dissolved in dry THF (500 ml) and cooled to −78° C. under N₂. n-BuLi (2.5M in hexanes, 50.6 ml, 0.126 mol) was added dropwise via syringe, and the reaction mixture stirred at −78° C. for 30 min. Methyl-3-[1-triphenylmethyl-1H-imidazol-4-yl]-propanoate (20 g, 50 mmol) was dissolved in 150 ml of dry THF and cooled to −78° C. under N₂. The sulfone anion solution was added to the THF solution of methyl ester via cannula (approximately 20 min), and the reaction mixture stirred for 1 hour after the addition was complete. The reaction was quenched by the addition of saturated solution of ammonium chloride (500 ml) and extracted with ethyl acetate (2×300 ml). The ethyl acetate layer was separated, dried over MgSO₄, filtered and evaporated in vacuo to afford a viscous yellow oil. The crude product was purified by silica gel column chromatography using ethyl acetate/hexanes to afford 32 g of a white solid, the racemic mixture of 1-[1-triphenylmethyl-1H-imidazol-4-yl]-4-p-toluenesulfonyl-6-cyclohexyl hexan-3-one.

1-[1-Triphenylmethyl-1H-imidazol-4-yl]-4-p-toluenesulfonyl-6-cyclohexyl hexan-3-one ¹H-NMR (300 MHz, CDCl₃): δ7.60 (d, J=8 Hz, 2H), 7.30 (m, 9H), 7.26 (d, J=8 Hz, 2H), 7.10 (m, 7H), 6.56 (s, 1H), 4.04 (dd, J=4.6 Hz, 1H), 3.14 (m, 1H), 2.97 (m, 1H), 2.78 (m, 2H), 2.40 (s, 3H), 1.82 (m, 2H), 1.56 (m, 6H), 1.07 (m, 5H), 0.72 (m, 2H). Mass Spectrum (DCl/NH₃): 645 (M+1), MW=644.8824, $C_{41}H_{44}N_2S_1O_3$.

Step 2

NaH (60% dispersion in mineral oil, 4.65 g, 0.116 mol) was suspended in dry THF (300 ml) and HMPA (54 ml) at 0° C. under N₂. 1-[1-Triphenylmethyl-1H-imidazol-4-yl]-4-p-toluenesulfonyl-6-cyclohexyl hexan-3-one (60 g, 0.093 mol) in dry THF (150 ml) was added via cannula to the NaH suspension. The reaction mixture was stirred for 30 min after the addition was complete. Diethyl chlorophosphate (16.15 ml, 0.112 mol) was added via syringe, and the reaction mixture left to stir at room temperature for 24 hours. The reaction was quenched by the addition of saturated solution of ammonium chloride (500 ml) and extracted with ethyl acetate (2×500 ml). The ethyl acetate layer was separated, washed with water (2×500 ml), followed by washing with brine. The ethyl acetate layer was dried over $MgSO_4$, filtered and evaporated in vacuo to afford a viscous yellow oil. The crude oil was purified by passing through a pad of silica gel (200 g) using approximately 1.5 liters of ethyl acetate/hexanes 2:8. The ethyl acetate/hexanes filtrate was evaporated in vacuo and the solid remaining was triturated with dry ether (150 ml), filtered and washed with ether to give 33 g of a crystalline white solid (first crop). The filtrate was once again evaporated in vacuo to give additional solid which again was triturated with ether to give after filtration 11.27 g of white solid (second crop). Repeating this sequence one more time gave an additional 3.88 g for a combined total of 48.15 g (67%) of white solid, 1-[1-triphenylmethyl-1H-imidazol-4-yl]-3-(diethoxylphosphinyl)oxy-4-p-toluenesulfonyl-6-cyclohexyl-3-hexene.

1-[1-Triphenylmethyl-1H-imidazol-4-yl]-3-(diethoxylphosphinyl)oxy-4-p-toluenesulfonyl-6-cyclohexyl-3-hexene $^1$H-NMR (300 MHz, $CDCl_3$): δ7.72 (d, J=7 Hz, 2H), 7.30 (m, 9H), 7.14 (d, J=7 Hz, 2H), 7.08 (m, 7H), 6.47 (s, 1H), 4.14 (Overlapping quartets, 4H), 2.74 (m, 4H), 2.34 (s, 3H), 2.26 (m, 2H), 1.64 (m, 5H), 1.40-1.02 (m, 6H), 1.26 (t, 6H), 0.86 (m, 2H).

Step 3

1-[1-Triphenylmethyl-5-imidazoyl]-3-(diethoxyphosphinyl)oxy-4-p-toluenesulfonyl-6-cyclohexyl-3-hexene (14.5 g, 0.018 mol) was dissolved in dry THF (150 ml) and HMPA (10 ml) at room temperature under $N_2$. $SmI_2$ (0.1M solution in THF) was added to the reaction in 50 ml portions via syringe. A total of 400 ml of 0.1M $SmI_2$ was added. After the last 50 ml portion was added, the blue reaction mixture was stirred for 1 hour. The reaction mixture was added to 500 ml of a saturated solution of ammonium chloride and extracted with ethyl acetate (2×500 ml). The ethyl acetate layer was washed with brine (250 ml), water (2×400 ml) and brine (250 ml). The ethyl acetate layer was separated, dried over $MgSO_4$, filtered and evaporated in vacuo to give a yellow oil. The crude acetylene was taken up in 25 ml of $CHCl_3$ and filtered through a pad of silica gel (200 g) using 1 liter of ethyl acetate/hexanes (2:8). The filtrate was evaporated in vacuo to afford a viscous yellow oil which solidified upon standing. The solid was triturated with hexanes, filtered and washed with hexanes to give 5.5 g of 1-[1-triphenylmethyl-1H-imidazol-4-yl]-6-cyclohexyl-3-hexyne.

1-[1-Triphenylmethyl-1H-imidazol-4-yl]-6-cyclohexyl-3-hexyne $^1$H NMR (300 MHz, $CDCl_3$): δ7.30 (m, 9H), 7.12 (m, 7H), 6.60 (m, 1H), 2.70 (m, 2H), 2.42 (m, 2H), 2.06 (m, 2H), 1.64 (m, 5H), 1.34–1.04 (m, 6H), 0.82 (m, 2H); Mass Spectrum (DCl/$NH_3$): 473 (M+1)$^+$, MW=472.6754, $C_{34}H_{36}N_2$ CHN: Calc.: C: 86.39, H: 7.67, N: 5.92; Found: C: 85.82, H: 7.73, N: 5.79.

Step 4

1-[1-Triphenylmethyl-1H-imidazol-4-yl]-6-cyclohexyl-3-hexyne (0.30 gram, 0.64 mmol) was dissolved in ethanol (10 ml). 2N HCl (20 ml) was added, and the mixture heated at 90° C. for 1 hour. The reaction mixture was cooled, filtered, and the filtrate neutralized with 10% NAOH solution and then partitioned between chloroform and water. The chloroform layer was separated, dried over $Na_2SO_4$, filtered and evaporated in vacuo to obtain the crude oil. The crude product was purified using column chromatography using MeOH/$CHCl_3$, 10:90 to afford 155 mgs of 1-[1H-imidazol-4-yl]-6-cyclohexyl-3-hexyne (23).

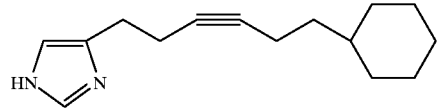

23

4-(6-Cyclohexylhex-3-ynyl)imidazole (23) $^1$H-NMR (300 MHz, $CDCl_3$): δ7.05 (s, 1H), 6.83 (s, 1H), 2.80 (m, 2H), 2.45 (m, 2H), 2.15 (m, 2H), 1.68 (m, 5H), 1.4–1.1 (m, 6H), 0.86 (m, 2H); Mass Spectrum: (DCl/$NH_3$): 231 (M+1)$^+$, MW=230.3434, $C_{15}H_{22}N_2$. CHN Analysis: Calc.: C: 78.26, H: 9.56, N: 12.17; Found: C: 77.79, H: 9.51, N: 11.86.

EXAMPLE 24

Preparation of 1-[1H-imidazol-4-yl]-6-cyclohexyl-cis-3-hexene (4-(6-cyclohexylhex-cis-3-enyl)imidazole)

Step 1

1-[1-Triphenylmethyl-1H-imidazol-4-yl]-6-cyclohexyl-3-hexyne (6.8 g, 0.014 mol) was dissolved in dry ethyl acetate (100 ml). Lindlar catalyst (5%, 1.8 g Pd on $CaCO_3$ poisoned with lead) and 15 mgs of quinoline were added. $H_2$ was added to the reaction flask via a balloon. The reaction flask was evacuated and then refilled with $H_2$ gas from the balloon 3 times. The reaction was left to stir at room temperature under the presence of $H_2$ (1 atm) for 48 hours. The $H_2$ gas was removed and the reaction mixture filtered through a pad of celite with ethyl acetate, the ethyl acetate was removed in vacuo to afford 6.75 g of 1-[1-triphenylmethyl-1H-imidazol-4-yl]-6-cyclohexyl-cis-3-hexene.

1-[1-Triphenylmethyl-1H-imidazol-4-yl]-6-cyclohexyl-cis-3-hexene $^1$H-NMR (300 MHz, $CDCl_3$): δ7.30 (m, 9H), 7.12 (m, 7H), 6.50 (s, 1H), 5.31 (m,2H), 2.57 (m, 2H), 2.34 (m, 2H), 1.96 (m, 2H), 1.64 (m, 5H), 1.50 (m, 6H), 0.82 (m, 2H); Mass Spectrum: (DCl/$NH_3$): 475 (M+1)$^+$, MW=474.6914, $C_{34}H_{38}N_2$.

Step 2

1-[1-Triphenylmethyl-1H-imidazol-4-yl]-6-cyclohexyl-cis-3-hexene (1 gram, 2.12 mmol) was dissolved in ethanol (20 ml). 2N HCl (60 ml) was added and the mixture heated at 90° C. for 1 hour. The reaction mixture was cooled, filtered and the filtrate neutralized with 10% NaOH solution and then partitioned between $CHCl_3$ and water. The chloroform layer was separated, dried over $Na_2SO_4$, filtered and evaporated in vacuo to obtain the crude oil. The crude product was purified by silica gel column chromatography using MeOH/$CHCl_3$, (10:90) to afford 475 mgs of 1-[1H-imidazol-4-yl]-6-cyclohexyl-cis-3-hexene (24).

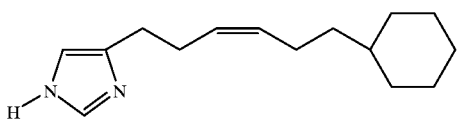

4-(6-Cyclohexyl-cis-3-enyl)imidazole (24) $^1$H-NMR (300 MHz, CDCl$_3$): δ7.52 (s, 1H), 6.76 (s, 1H), 5.38 (m, 2H), 2.65 (m, 2H), 2.36 (m, 2H), 1.98 (m, 2H), 1.64 (m, 5H), 1.22 -1.08 (m, 6H), 0.84 (m, 2H); Mass Spectrum (DCl/NH$_3$): 233 (M+1)$^+$, MW=232.3704, C$_{15}$ H$_{24}$ N$_2$; CNH Analysis: Calc.: C: 77.58, H: 10.34, N: 12.06; Found: C: 76.14, H: 10.04, N: 11.95.

EXAMPLE 25

Preparation of 1-[1H-imidazol-4-yl]-6-cyclohexyl-trans -3-hexene (4-(6-cyclohexyhex-trans-3-enyl) imidazole)

Step 1

3-Cyclohexylpropyl-p-toluene-sulfone (0.42 g, 1.57 mmol) was dissolved in dry THF (15 ml) and cooled to −78° C. under N$_2$. Sodium bis(trimethylsilyl) amide (1.0 M in THF, 1.70 ml, 1.70 mmol) was added via syringe, and the reaction stirred at −78° C. for 1 hour. 3-[1-Triphenylmethyl-1H-imidazol-4-yl]-propanal (0.577 g, 1.57 mmol) in dry THF (25 ml) was added dropwise to the yellow green sulfone anion solution and the reaction stirred for an additional 30 min. The reaction was quenched saturated solution of ammonium chloride (200 ml) and extracted with ethyl acetate (250 ml). The ethyl acetate layer was separated, dried over MgSO$_4$, filtered and evaporated in vacuo to give a yellow oil. The crude product was purified by silica gel column chromatography using ethyl acetate/hexanes to afford 226 mgs of a racemic mixture of 1-[1-triphenylmethyl-1H-imidazol-4-yl]-3-hydroxy-4-phenylsulfonyl-6-cyclohexyl-hexane.

1-[1-Triphenylmethyl-1H-imidazol-4-yl]-3-hydroxy-4-phenylsulfonyl-6-cyclohexyl-hexane $^1$H-NMR (300 MHz, CDCl$_3$): δ7.88 (m, 2H), 7.58 (m, 1H), 7.50 (m, 2H), 7.30 (m, 9H), 7.27 (m, 1H), 7.10 (m, 6H), 6.55 (2X s, 1H), 4.26 (m, 1H), 4.16 (m, 1H), 3.18 (m, 1H), 2.88 (m, 1H), 2.66 (m, 1H), 2.10 (m, 1H), 1.80 (m, 5H), 1.10 (m, 6H), 0.76 (m, 2H).

Step 2

1-[1-Triphenylmethyl-1H-imidazol-4-yl]-3-hydroxy-4-phenylsulfonyl-6-cyclohexyl-hexane (0.226 g, 0.375 mmol) was dissolved in dry MEOH (20 ml). NaH$_2$PO$_4$ (0.30 g) was added and the reaction mixture placed under N$_2$. Na(Hg) (2% by weight, total of 7 g) was added to the reaction mixture which was stirred for 1.5 hours. The reaction mixture was filtered through a pad of celite, washing the celite with MeOH (20 ml) and ethyl acetate (100 ml). The filtrate was evaporated in vacuo, and the residue partitioned between CHCl$_3$ and water (50/50 ml). The CHCl$_3$ layer was separated, dried over MgSO$_4$, filtered, and evaporated in vacuo. The pale yellow oil was purified by thin layer chromatography using ethyl acetate/hexanes 3:7 to afford 57 mgs of 1-[1-triphenylmethyl-1H-imidazol-4-yl]-6-cyclohexyl-trans-3-hexene and 30 mgs of of 1-[1-triphenylmethyl-1H-imidazol-4-yl]-6-cyclohexyl-cis-3-hexene.

1-[1-Triphenylmethyl-1H-imidazol-4-yl]-6-cyclohexyl-trans-3-hexene $^1$H-NMR (300 MHz, CDCl$_3$): δ7.30 (m, 9H), 7.12 (m, 7H), 6.48 (s, 1H), 5.36 (m,2H), 2.57 (m, 2H), 2.26 (m, 2H), 1.92 (m, 2H), 1.64 (m,5H), 1.16 (m, 6H), 0.82 (m, 2H).

1-[1-Triphenylmethyl-1H-imidazol-4-yl]-6-cyclohexyl-cis-3-hexene $^1$H-NMR (300 MHz, CDCl$_3$): δ7.30 (m, 9H), 7.12 (m, 7H), 6.49 (s, 1H), 5.32 (m, 2H), 2.56 (m, 2H), 2.32 (m, 2H), 1.95 (m, 2H), 1.64 (m, 5H), 1.16 (m, 6H), 0.82 (m, 2H).

Mass Spectrum: (DCl/NH$_3$): trans-isomer and cis-isomer 475 (M+1)$^+$, MW=474.6914, C$_{34}$H$_{38}$ N$_2$.

Step 3

1-[1-Triphenylmethyl-1H-imidazol-4-yl]-6-cyclohexyl-trans-3-hexene (0.057 g, 0.12 mmol) was dissolved in ethanol (2 ml). 2N HCl (15 ml) was added and the reaction mixture heated at 90° C. for 1 hour. The reaction mixture was cooled, filtered and the organic volatiles evaporated in vacuo. The residue was partitioned between CHCl$_3$ and 10% NaOH solution. The CHCl$_3$ layer was separated, dried over MgSO$_4$, filtered and evaporated in vacuo to give a crude yellow oil. The crude product was purified using silica gel column chromatography using CHCl$_3$/MeOH (90:10) to give 19 mgs of a yellow oil, 1-[1H-imidazol-4-yl]-6-cyclohexyl-trans-3-hexene (25).

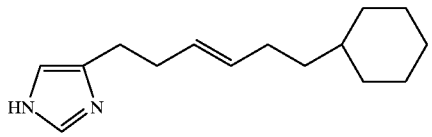

4-(6-Cyclohexylhex-trans-3-enyl)imidazole (25) $^1$H-NMR (300 MHz, CDCl$_3$): δ7.56 (s, 1H), 6.76 (s, 1H), 5.43 (m, 2H), 2.64 (m, 2H), 2.30 (m, 2H), 1.96 (m, 2H), 1.65 (m, 5H), 1.18 (m, 6H), 0.83 (m, 2H); Mass Spectrum (DCl/NH$_3$): 233 (M+1)$^+$, MW=232.3704, C$_{15}$H$_{24}$N$_2$.

EXAMPLE 26

Preparation of 1-[1H-imidazol-4-yl]-5-amino-6-cyclohexyl-trans-3-hexene (1-cyclohexyl-6-imidazol-4-ylhex-trans-3-en-2-(S)-ylamine)

Step 1

3-Cyclohexyl-1-N-BOC-amino-propyl-phenyl sulfone (3.5 g, 9.17 mmol) was dissolved in dry THF (80 ml) and cooled to −78° C. under N$_2$. n-BuLi (2.5 M in hexanes, 8.07 ml, 20.17 mmol) was added dropwise via syringe, and the reaction mixture stirred for 1 hour. 3-[1-Triphenylmethyl-1H-imidazol-4-yl]-propanal (3.35 g, 9.17 mmol) was dissolved in dry THF (80 ml) and added to the THF solution of sulfone slowly via syringe. The reaction mixture was stirred for 1 hour after the addition was complete. The reaction was quenched by the addition of saturated solution of ammonium chloride (300 ml) and extracted with ethyl acetate (2×100 ml). The ethyl acetate layer was separated, dried over MgSO$_4$, filtered and evaporated in vacuo to afford a viscous yellow oil. The crude product was purified by silica gel column chromatography using ethyl acetate/hexanes (4:6), to give 3.7 g of a white solid, the racemic mixture of 1-[1-triphenylmethyl-1H-imidazol-4-yl]-3-hydroxy-4-phenylsulfonyl-5-N-BOC-amino-6-cyclohexyl hexane.

1-[1-Triphenymethyl-1H-imidazol-4-yl]-3-hydroxy-4-phenylsulfonyl-5-N-BOC-amino-6-cyclohexyl hexane $^1$H NMR (300 MHz, CDC$_{l3}$): δ7.90 (m, 2H), 7.52 (m, 3H), 7.31 (m, 9H), 7.10 (m, 7H), 6.51 (m, 1H), 5.8 (d, 1H), 4.35 (m, 2H), 3.2 (m, 1H), 2.65 (m, 2H), 2.2 -1.0 (m, 14H), 0.82 (m, 2H).

Step 2

1-[1-Triphenymethyl-1H-imidazol-4-yl]-3-hydroxy-4-phenylsulfonyl-5-N-BOC-amino-6-cyclohexyl hexane (3.7 g, 4.95 mmol) was dissolved in dry methanol. Sodium hydrogen phosphate monobasic (4.92 g, 34.6 mmol) was added and the reaction mixture cooled to 0° C. under N$_2$. 2% Na(Hg) (2×12 g) was added and the reaction stirred for 1.5 hours. After that time, a second portion of Na(Hg) (24 g) was added and the reaction mixture stirred for an additional 1 hour, warming to room temperature. The reaction mixture was filtered through a pad of celite, washing the pad with ethyl acetate (300 ml). The filtrate was evaporated in vacuo and the residue remaining partitioned between CHCl$_3$ and water. The CHCl$_3$ layer was separated, dried over MgSO$_4$, filtered and concentrated to give a yellow oil. The crude product was purified by silica gel column chromatography using ethyl acetate/hexanes (3:7) to give 1.5 g of an oil, 1-[1-triphenymethyl-1H-imidazol-4-yl-5-N-BOC-amino-6-cyclohexyl-3-hexene.

1-[1-Triphenymethyl-1H-imidazol-4-yl]-5-N-BOC-amino-6-cyclohexyl-3-hexene $^1$H-NMR (300 MHz, CDCl$_3$): δ7.31 (m, 9H), 7.12 (m, 7H), 6.50 (s, 1H), 5.56 (m, 1H), 5.30 (m, 1H), 2.58 (m, 2H), 2.32 (m, 2H), 1.78 -1.52 (m, 12H), 1.4 (m, 6H), 1.18 (m, 4H), 0.86 (m, 2H).

Step 3

1-[1-Triphenymethyl-1H-imidazol-4-yl]-5-N-BOC-amino-6-cyclohexyl-3-hexene (1.5 g, 2.54 mmol) was dissolved in ethanol (15 ml). 2N HCl (50 ml) was added and the reaction mixture heated at 90° C. for 1 hour. The reaction was cooled, filtered and the filtrate neutralized to pH=7–8 with 10% NaOH solution, and then extracted with CHCl$_3$. The CHCl$_3$ layer was separated, dried over MgSO$_4$, filtered and evaporated in vacuo to give a crude yellow oil. The crude product was purified by silica gel column chromatography using CHCl$_3$/MeOH/NH$_4$OH (90:10:1) to afford 512 mgs of 1-[1H-imidazol-4-yl]-5-amino-6-cyclohexyl-trans-3-hexene (26).

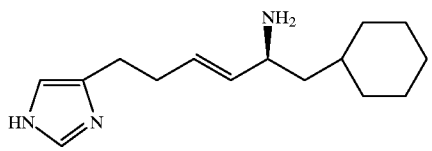

26

1-Cyclohexyl-6-imidazol-4-ylhex-trans-3-en-2-(S)-ylamine (26) $^1$H-NMR (300 MHz, CDCl$_3$): δ7.52 (s, 1H), 6.75 (s, 1H), 5.54 (m, 1H), 5.36 (m, 1H), 3.12 (m, 1H), 2.68 (m, 2H), 2.34 (m, 2H), 1.64 (m, 4H), 1.32-1.06 (m, 6H), 0.87 (m, 2H); Mass Spectrum (DCl/NH$_3$): 248 (M+1)$^+$, MW=247.3852, C$_{15}$H$_{25}$N$_3$.

EXAMPLE 27

Preparation of 4-hex-3-ynylimidazole n-BuLi (2.5 M, 0.24 mL, 1.1 eq) was added to TMEDA (0.092 mL, 1.1 eq) at 0° C. The mixture was stirred at 0 ° C. for 30 min and cooled to −20° C. A solution of acetylene (26) (0.20 g, 1 eq) in anhyd. tetrahydrofuran (2 mL) was added.

After 45 min at room temperature a solution of iodoethane (0.129 g, 1.5 eq) in anhyd. tetrahydrofuran (1 mL) was added. The reaction mixture was stirred at 50° C. for 24–36 hours. The reaction mixture was treated with water and extracted with ethyl acetate. The organic layer was separated, washed with water and dried over anhydrous sodium sulfate. Removal of the solvent gave crude product which was purified by flash column chromatography (eluted with ethyl acetate:hexanes (1:1) to afford pure alkylated acetylene product 0.175 g. Deprotection of the trityl group of 100 mg of this product using HCl (2N at 80° C.) gave 4-hex-3-ynylimidazole (40 mg).

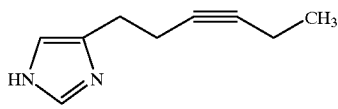

27

4-Hex-3-ynylimidazole (27) $^1$H-NMR (300 MHz, CDCl$_3$): δ7.54 (s, 1H), 6.83 (s, 1H), 2.80 (t, J=7.2 Hz, 2H), 2.45 (m, 2H), 2.15 (m, 2H), 1.08 (t, J=7.2 Hz, 3H); $^{13}$C NMR (300 MHz, CDCl$_3$) δ134.4, 118.0, 82.5, 79.0, 69.0, 26.5, 19.2, 14.2, 12.4; Mass Spectrum (Cl) m/e 149(M+1).

EXAMPLE 28

Preparation of 4-heptyl-3-ynylimidazole

4-Heptyl-3-ynylimidazole was prepared as described in example 27 except 1-iodopropane was used.

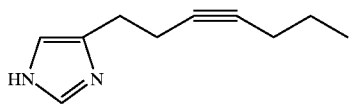

28

4-Heptyl-3-ynylimidazole (28) $^1$H-NMR (300 MHz, CDCl$_3$): δ7.68 (s, 1H), 6.85 (s, 1H), 3.73 (brs, 1H), 2.79 (m, 2H), 2.47 (t, J=7.2 Hz, 2H), 2.10 (t, J=7.2 Hz, 2H), 1.46 (m, 2H), 0.93 (t, J=7.2 Hz, 3H); $^{13}$C NMR (300 MHz, CDCl$_3$) δ135.2, 134.4, 118.0, 81.0, 79.7, 68.9, 26.6, 22.4, 20.7, 19.2, 13.4; Mass Spectrum (Cl) m/e 163(M+1).

EXAMPLE 29

Preparation of 4-(7-methyloct-3-ynyl)imidazole 4-(7-Methyloct-3-ynyl)imidazole was prepared as described in example 27 except 1-iodo-3-methylbutane was used.

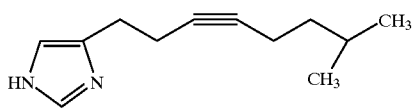

29

4-(7-Methyloct-3-ynyl)imidazole (29) Rf 0.3 (EtOAc:MeOH (95:5)); $^1$H-NMR (300 MHz, CDCl$_3$): δ7.68 (s, 1H), 6.85 (s, 1H), 5.96 (brs, 1H), 2.79 (t, J=7.2 Hz, 2H), 2.45 (t, J=7.2 Hz, 2H), 2.12 (t, J=7.5 Hz, 2H), 1.37 (m, 1H), 0.85 (d, J=6.9 Hz, 6H); Mass Spectrum (Cl) m/e 191(M+1).

EXAMPLE 30

Preparation of 4-(6-cyclopentylhex-3-ynyl)imidazole 4-(6-Cyclopentylhex-3-ynyl)imidazole was prepared in the same manner as described in example 27 except cyclopentyl ethyl iodide was used.

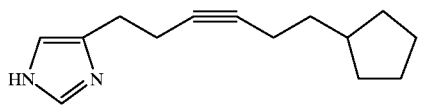

30

4-(6-Cyclopentylhex-3-ynyl)imidazole (30) Rf 0.4 (EtOAC:MeOH(95:5)); $^1$H-NMR (300 MHz, CDCl$_3$): δ7.57 (s, 1H), 6.84 (s, 1H), 2.79 (t, J=7.2 Hz, 2H), 2.46 (t, J=7.2 Hz, 2H), 2.15 (t, J=7.2 Hz, 2H), 1.0-1.80 (m, 11H); Mass Spectrum (Cl) m/e 217(M+1).

EXAMPLE 31

Preparation of 4-(8-phenyloct-3-ynyl)imidazole 4-(8-Phenyloct-3-ynyl)imidazole was prepared in the same manner as described in example 27 except 4-phenyl-1-iodobutane was used.

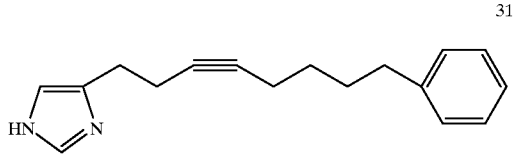

31

4-(8-Phenyloct-3-ynyl)imidazole (31) Rf 0.5 (EtOAC:MeOH(95:5)); $^1$H NMR (300 MHz, CDCl$_3$): δ7.24 (s, 1H), 7.17 (m, 2H), 7.23 (m, 3H), 6.79 (s, 1H), 2.77 (t, J=6.9 Hz, 2H), 2.59 (t, J=7.2 Hz, 2H), 2.46 (m, 2H), 2.16 (m, 2H), 1.67 (m, 2H), 1.50 (m, 2H); Mass Spectrum (Cl) m/e 253(M+1).

EXAMPLE 32

Preparation of 4-(7,7-dimethyloct-3-ynyl)imidazole 4-(7,7-Dimethyloct-3-ynyl)imidazole was prepared in the same manner as described in example 27 except 3,3-dimethyl-butyl iodide was used.

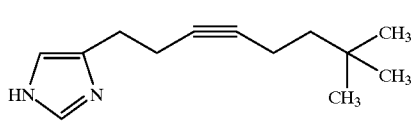

32

4-(7,7-Dimethyloct-3-ynyl)imidazole (32) Rf 0.5 (EtOAC:MeOH(95:5)); $^1$H-NMR (300 MHz, CDCl$_3$): δ7.70 (s, 1H), 6.86 (s, 1H), 2.80 (t, J=6.9 Hz, 2H), 2.47 (t, J=7.2, 2H), 2.09 (m, 2H), 1.42 (m, 2H), 0.85 (s, 9H); Mass Spectrum (Cl) m/e 205(M+1).

EXAMPLE 33

Preparation of 4-non-3-ynylimidazole

4-Non-3-ynylimidazole was prepared in the same manner as described in example 27 except 1-iodopentane was used.

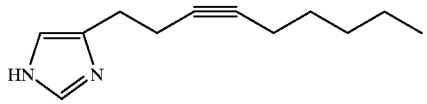

33

4-Non-3-ynylimidazole (33) $^1$H-NMR (300 MHz, CDCl$_3$): δ7.57 (s, 1H), 6.84 (s, 1H), 2.79 (t, J=7.2 Hz, 2H), 2.48 (t, J=7.2 Hz, 2H), 2.14 (t, J=7.2 Hz, 2H), 1.43 (m, 2H), 1.30 (m, 4H), 0.87 (t, J=7.2 Hz, 3H); $^{13}$C NMR (300 MHz, CDCl$_3$) δ135.5, 134.2, 118.1, 81.0, 79.5, 31.06, 28.7, 26.3, 22.2, 19.1, 18.7, 13.9; Mass Spectrum (Cl) m/e 191(M+1).

EXAMPLE 34

Preparation of 4-undec-3-ynylimidazole

4-Undec-3-ynylimidazole was prepared in the same manner as described in example 27 except 1-iodoheptane was used.

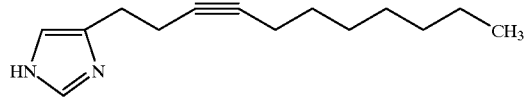

34

4-Undec-3-ynylimidazole (34) $^1$H-NMR (300 MHz, CDCl$_3$): δ7.56 (s, 1H), 6.83 (s, 1H), 2.78 (t, J=7.2 Hz, 2H), 2.46 (m, 2H), 2.13 (m, 2H), 1.46 (m, 2H), (1.25 (m, 8H), 0.86 (t, J=6.9 Hz, 3H); Mass Spectrum (Cl) m/e 219(M+1).

EXAMPLE 35

Preparation of 4-(6-imidazol-4-ylhex-3-ynyl) morpholine 4-(6-lmidazol-4-ylhex-3-ynyl)morpholine was prepared in the same manner as described in example 27 except 4-(2-iodoethyl)morpholine was used.

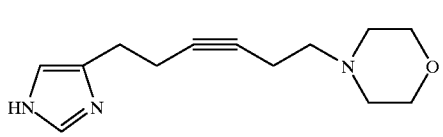

35

4-(6-Imidazol-4-ylhex-3-ynyl)morpholine (35) $^1$H-NMR (300 MHz, CDCl$_3$): δ7.70 (s, 1H), 6.90 (s, 1H), 3.97 (t, J=6.6 Hz, 2H), 3.68 (t, J=4.8 Hz, 4H), 2.80 (t, J=7.2 Hz, 2H), 2.62 (t, J=6.6 Hz, 2H), 2.51 (m, 2H), 2.45 (m, 4H); Mass Spectrum (Cl) m/e 234 (M+1).

EXAMPLE 36

Preparation of 4-(5-cyclohexylpent-1-ynyl) imidazole n-BuLi (2.5 M in hexane, 0.192 ml, 00.48 mmol) was added to a solution of 4-(2,2-dibromovinyl)-1-(triphenylmethyl)imidazole (108 mg, 0.22 mmol) in THF (5 ml), which had been cooled to −78° C. under N$_2$. After 30 min, a solution of 3-cyclohexylpropyl iodide (0.063 g, 0.25 mmol) in toluene (2 ml) was added. The reaction mixture was stirred at −78° C. for 20 min and at room temperature for 2 hours. The reaction mixture was quenched by the addition of saturated ammonium chloride solution (50 ml) and extracted with ethyl acetate (50 ml). The ethyl acetate layer was separated, dried over anhydrous sodium sulfate, filtered and concentrated. Purification using flash chromatography gave 182 mgs, (yield 40%) of the trityl protected imidazole. This was deprotected using 2N HCl at 90° C. to give 97 mg of final product.

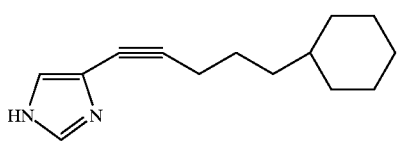

4-(5-Cyclohexylpent-1-ynyl)imidazole (36) $^1$H-NMR (300 MHz, CD$_3$OD): δ8.84 (s, 1H), 7.65 (s, 1H), 2.48 (t, J=6.9 Hz, 2H), 1.00-1.80 (m, 15H), Mass Spectrum (Cl) m/e 217 (M+1).

EXAMPLE 37

Preparation of 4-(7-cyclohexylhept-3-ynyl) imidazole 4-(7-Cyclohexylhept-3-ynyl)imidazole was prepared in the same manner as described in example 36 except that 4-(4,4-dibromobut-3-enyl)-1-(triphenylmethyl)imidazole was used.

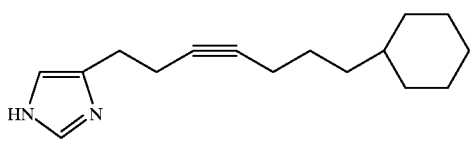

4-(7-Cyclohexylhept-3-ynyl)imidazole (37) $^1$H-NMR (300 MHz, CD$_3$OD): δ8.80 (s, 1H), 7.40 (s, 1H), 2.95 (t, J=6.9 Hz, 2H), 2.48 (m, 2H), 2.10 (m, 2H), 1.00-1.80 (m, 15H), Mass Spectrum (Cl) m/e 245 (M+1).

EXAMPLE 38

Preparation of 4-(5-phenylpent-1-ynyl)imidazole 4-(5-Phenylpent-1-ynyl)imidazole was prepared in the same manner as described in example 36 except 1-bromo-3-phenylpropane was used as the alkyl coupling reagent.

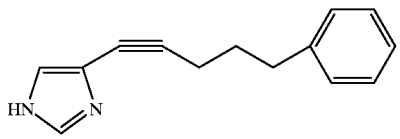

4-(5-Phenylpent-1-ynyl)imidazole (38) $^1$H-NMR (300 MHz, CD$_3$OD): δ8.85 (s, 1H), 7.70 (s, 1H), 7.20 (m, 5H), 2.80 (t, J=7.2 Hz, 2H), 2.50 (m, 2H), 1.95 (m, 2H), Mass Spectrum (Cl) m/e 211 (M+1).

EXAMPLE 39

Preparation of 4-(7-phenylhept-3-ynyl)imidazole 4-(7-Phenylhept-3-ynyl)imidazole was prepared in the same manner as described in example 36 except that 4-(4, 4-dibromobut-3-enyl)-1-(triphenylmethyl)imidazole and 1-bromo-3-phenylpropane were used.

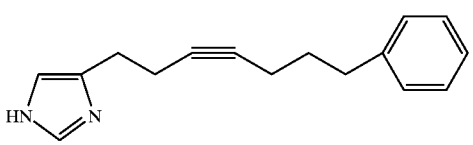

4-(7-Phenylhept-3-ynyl)imidazole (39) $^1$H-NMR (300 MHz, CD$_3$OD): δ8.80 (s, 1H), 7.40 (s, 1H), 7.20 (m, 5H), 2.95 (t, J=7.8 Hz, 2H), 2.60 (m, 2H), 2.15 (m, 2H), 1.75 (m, 2H), Mass Spectrum (Cl) m/e 239 (M+1).

EXAMPLE 40

Preparation of 4-oct-3-ynylimidazole

4-Oct-3-ynylimidazole was prepared in the same manner as described in example 27.

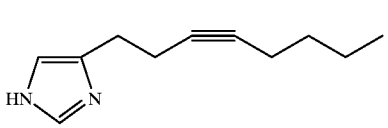

4-Oct-3-ynylimidazole (40) $^1$H-NMR (300 MHz, CDCl$_3$): δ7.69 (s, 1H), 6.84 (s, 1H), 2.80 (t, J=6.9 Hz, 2H), 2.48 (m, 2H), 2.12 (m, 2H), 1.39 (m, 2H), 0.88 (t, J=7.2 Hz, 3H).

EXAMPLE 41

Preparation of 4-(6-cyclohexylhexyl)imidazole

1-[1-Triphenylmethyl-1H-imidazol-4-yl]-6-cyclohexyl-3-hexyne (0.629 g, 1.33 mmol) was suspended in ethyl alcohol (3 ml). 2N HCl (25 ml) was added and the reaction mixture heated at 90° C. for 1 hr. The reaction mixture was cooled, filtered through a pad of celite and the filtrate evaporated in vacuo. The residue was dissolved in methanol (20 ml). 10% Pd(C) (0.139 g) and ammonium formate (1.5 g) were added, and the reaction mixture heated at 65° C. under N$_2$ for 6.5 hours. The reaction mixture was cooled, filtered through a pad of celite and the methanol filtrate concentrated. The residue was partitioned between CH$_2$Cl$_2$ and 10% NaOH solution (100 ml, 1:1). The CH$_2$Cl$_2$ layer was separated, washed with water (50 ml), dried over MgSO$_4$, filtered and evaporated in vacuo. Purification by flash chromatography using ethyl acetate as eluent gave 108 mgs of final product.

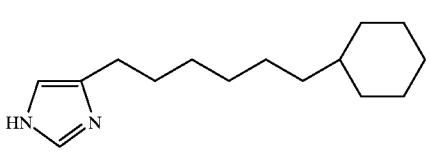

4-(6-Cyclohexylhexyl)imidazole (41) $^1$H-NMR (300 MHz, CD$_3$OD): δ7.53 (s, 1H), 6.73 (s, 1H), 2.56 (t, J=7.5 Hz, 2H), 1.65 (m, 7H), 1.40-1.10 (m, 12H), 0.89 (m, 2H); Mass Spectrum: (DCl/NH$_3$): 235 (M+1)$^+$.

EXAMPLE 42

Preparation of 4-(6-phenylhex-cis-3-enyl)imidazole

To a solution of (6) (109 mg, 0.30 mmol) and 3-phenylpropyltriphenylphosphonium bromide (0.138 g, 0.30 mmol) in THF (5 ml) at rt was added potassium tert-butoxide (1M in THF, 0.35 ml, 0.35 mmol). The reaction mixture was vigorously stirred for 3–4 hours at room temperature, quenched by the addition of water (10 ml) and extracted with dichlromethane (75 ml). The dichloromethane layer was separated, dried over anhydrous sodium sulfate, filtered and concentrated. The crude product was purified by flash chromatography using EtOAc:Hexanes (20:80) as the eluent to give a yellow oil. Deprotection in the usual manner gave final product.

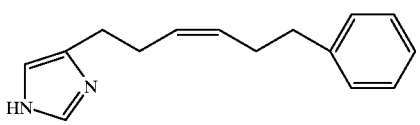

42

4-(6-Phenylhex-cis-3-enyl)imidazole (42) $^1$H-NMR (300 MHz, CD$_3$OD): δ8.80 (s, 1H), 7.20 (m, 6H), 6.40 (2t, 2H), 2.60 (m, 4H), 2.25 (m, 4H), Mass Spectrum (Cl) m/e 227 (M+1).

EXAMPLE 43

Preparation of 4-(2,2-dibromovinyl)-1-(triphenylmethyl)imidazole

Triphenylphosphine (5.24 g, 20.00 mmol) was added in portions over 20 min to a cooled (0° C.) solution of carbon tetrabromide (3.31 g, 10.00 mmol) in CH$_2$Cl$_2$ (40 ml). After 20 min, a solution of 1-[1-triphenylmethyl-1H-imidazol-4-yl]carboxaldehyde (1.69 g, 5.0 mmol) in CH$_2$Cl$_2$ (5 ml) was added dropwise over 10 min. After 3 hours the reaction was quenched by the addition of saturated sodium bicarbonate solution (100 ml) and ethyl acetate (200 ml). The ethyl acetate layer was separated, dried over sodium sulfate, filtered and concentrated. Purification using flash chromatography gave 1.9 g of product.

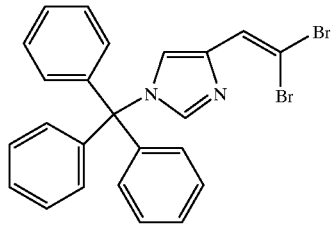

43

4-(2,2-Dibromovinyl)-1-(triphenylmethyl)imidazole (43) $^1$H-NMR (300 MHz, CDCl$_3$): δ7.05 (m, 6H), 7.35 (m, 10H), 7.45 (s, 1H), 7.43 (s, 1H), Mass Spectrum (Cl) m/e 495 (M+1).

EXAMPLE 44

Preparation of 4-(4,4-dibromobut-3-enyl)-1-(triphenylmethyl)imidazole 4-(4,4-Dibromobut-3-enyl)-1-(triphenylmethyl) imidazole was prepared in the same manner as in example 43 except triphenylmethyl-imidazole propanal was used.

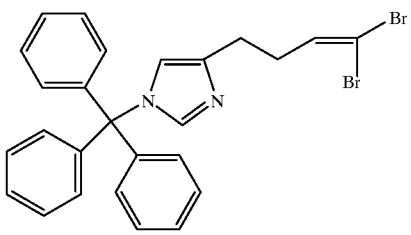

44

4-(4,4-Dibromobut-3-enyl)-1-(triphenylmethyl)imidazole (44) $^1$H-NMR (300 MHz, CDCl$_3$): δ7.40 (s, 1H), 7.05 (m, 6H), 7.35 (m, 9H), 6.58 (s, 1H), 6.38 (t, J=7.3, 1H), 2.70 (t, J=7.1Hz, 2H), 2.40 (q, J=7.5 Hz, 2H), Mass Spectrum (Cl) m/e 523 (M+1).

EXAMPLE 45

Preparation of 4-but-3-ynylimidazole

4-But-3-ynylimidazole HCl was prepared from the deprotection of compound 26 by treatment with 2N HCl.

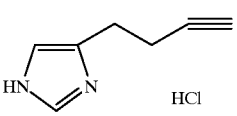

45

4-But-3-ynylimidazole (45) $^1$H-NMR (300 MHz, CD$_3$OD): δ8.90 (s, 1H), 7.40 (s, 1H), 2.95 (t, J=6.9 Hz, 2H), 2.60 (dt, J=2.4 and 6.9 Hz, 2H), 2.40 (t, J=2.7 Hz, 1H); Mass Spectrum (Cl) m/e 121 (M+1).

EXAMPLE 46

Preparation of 4-ethynylimidazole n-BuLi (0.192 ml, 0.48 mmol) was added to a solution of 4-(2,2-dibromovinyl)-1-(triphenylmethyl)imidazole (108 mg, 0.22 mmol) in THF (5 ml) at −78° C. under N$_2$. The reaction mixture was quenched by the addition of saturated ammonium chloride (50 ml) and extracted with ethyl acetate (75 ml). The ethyl acetate layer was washed with water (50 ml), separated, dried over anhydrous sodium sulfate, filtered and concentrated. Purification by flash chromatography gave 2[1-triphenylmethyl-1H-imidazol-4yl]ethyne, which was deprotected with 2N HCL to give 18 mg of final product.

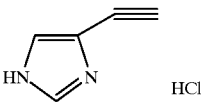

46

4-Ethynylimidazole (46) $^1$H-NMR (300 MHz, CD$_3$OD): δ8.94 (s, 1H), 7.80 (s, 1H), 4.20 (s,1H); Mass Spectrum (Cl) m/e 93 (M+1).

EXAMPLE 47

Preparation of 4-(4,4-dibromobut-3-enyl)imidazole 4-(4,4-dibromobut-3-enyl)imidazole was prepared by deprotection of 4-(4,4-dibromobut-3-enyl)-1-(triphenylmethyl)imidazole by HCl.

47

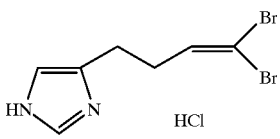

4-(4,4-Dibromobut-3-enyl)imidazole (47) $^1$H-NMR (300 MHz, CD$_3$OD): δ8.92 (s, 1H), 7.60 (s, 1H) 6.60 (t, J=7.2 Hz, 1H), 2.95 (t, J=7.2 Hz, 2H), 2.50 (t, J=7.5 Hz, 2H); Mass Spectrum (Cl) m/e 281 (M+1).

EXAMPLE 48

Preparation of 4-(2,2-dibromovinyl)imidazole 4-(2,2-dibromovinyl)imidazole HCl was prepared by deprotection of compound 43 by treatment with HCl.

48

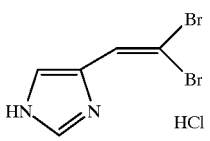

4-(2,2-Dibromovinyl)imidazole (48) $^1$H-NMR (300 MHz, CD$_3$OD): δ8.98 (s, 1H), 8.18 (s, 1H), 7.60 (s, 1H); Mass Spectrum (Cl) m/e 251 (M+1).

Other similar compounds may also be prepared by the processes of the present invention. Representative such compounds include:

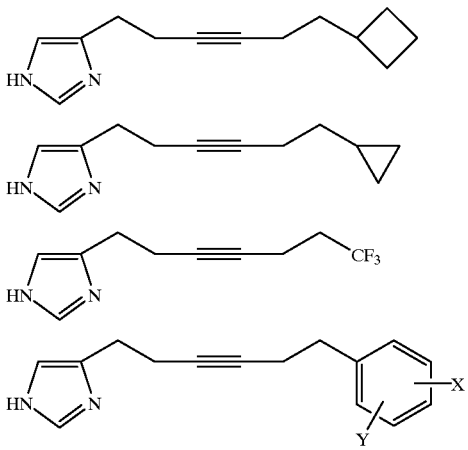

where X and Y can be: F, Cl, Br, I, H, alkyl, substituted alkyl such as tert-butyl, OCH$_3$, N(CH$_3$)$_2$, CF$_3$, NO$_2$, CN, or OR$_6$, where R$_6$ can be phenyl, substituted phenyl, heterocyclic, alkyl, or substituted alkyl.

X and Y can denote either or any combination of ortho-, meta- or para-substitution of the phenyl ring.

The compounds of this invention are antagonists of the histamine H$_3$ receptor. The binding affinity of the compounds of the invention to the H$_3$ receptor may be demonstrated by the procedure described below:

In Vitro Histamine H$_3$ Receptor Binding Analysis.

Histamine H$_3$ receptor affinity was determined in rat cortical membranes using the H$_3$ selective agonist ligand, [$^3$H]-Nα-methylhistamine (78.9 Ci/mmole, DuPont NEN Research Products, Boston, Mass.) according to the method of West et al. (1990) with modifications. Briefly, animals were sacrificed by decapitation and the cerebral cortex was rapidly removed. Rat cortices were mechanically homogenized with an Omni 1000 motor driven homogenizer in 10 volumes (wt/vol) of Krebs-Ringers Hepes buffer (pH 7.4) containing the following protease inhibitors; EDTA (10 mM), PMSF (0.1 mM), chymostatin (0.2 mg/50 ml) and leupeptin (0.2 mg/50 ml). The homogenate was centrifuged in a Sorvall at ~40,000×g for 30 min. The pellet was resuspended by mechanical homogenization in 25 ml water and lysed on ice for 30 min. The homogenate was recentrifuged and the membrane lysis was repeated. The membranes were recentrifuged and the final pellet was resuspended in 14 volumes of water to give approximately 200 μg protein/ 100 μl final concentration. The suspension was stored at −80° C. prior to use. Protein concentrations were determined by Coomassie Plus Protein Assay (Pierce, Rockford, Ill.).

The binding assay was carried out in polypropylene tubes in a total volume of 0.4 ml of 50 mM Na$^+$ Phosphate buffer (pH 7.4), containing 150–200 μg of tissue protein, 0.8–1.2 nM [$^3$H]-Nα-methylhistamine and 0.3 to 10,000 nM GT-2016. Nonspecific binding (NSB) was accounted for by the inclusion of thioperamide (10 μM). The samples were incubated for 40 min at 25° C. Samples were filtered through glass fiber strips, pre-washed with 0.3% polyethyleneimine, using a Brandell cell harvester. The filters were rapidly washed three times with 4 ml of 25 mM Tris buffer containing 145 mM NaCl (pH 7.4, 4° C.). Filters were transferred to polyethylene minivials and counted in 3.5 ml of scintillation fluid (Ecolume, ICN Biomedicals, Inc.). Using this procedure, the non-specific binding was less than 10% of the total binding and the binding to the glass fiber filters was negligible. Saturation and competition experiments were analyzed with the ReceptorFit saturation and competition curve fitting programs (Lundon Software, Inc., Cleveland, Ohio). K$_i$'s were determined using the equation K$_i$=IC$_{50}$/(1+([Ligand]/[K$_d$]). The results are given in Table 1.

Results

The results of the H$_3$ receptor binding assay has revealed several novel potent H$_3$ receptor ligands as depicted in Table 1. Importantly, these data demonstrate a stereoselective bias for the H$_3$ receptor in compounds with a chiral center at the 5-carbon position distal to the imidazole ring. While H$_3$ agonists (R-α-methylhistamine, α, β-dimethyl histamine) have been used to illustrate the stereochemical bias that the H$_3$ receptor can recognize, none of those compounds contain any stereochemical center beyond the equivalent 1 or 2 carbon centers distal to the imidazole head. Moreover, the importance of H$_3$ antagonists with a stereochemical preference has not been reported. This was clearly illustrated in the synthesis and direct comparisons of compounds 1 versus 4. Moreover, the importance of the chiral center on H$_3$ receptor affinity can be seen with the NH$_2$ substitution of the C-5 carbon in compound 26 versus 25.

Additonally, the development of 3,4 substituted acetylene and olefin analogs provides a novel series of H$_3$ ligands with high affinity for the H$_3$ receptor. The specificity of the position of the 3, 4 unsaturated carbon linkage for potent H$_3$ receptor activity was clearly demonstrated by comparison with the 1,2 unsaturated analogs 36 and 38. More surprising, is the development of the acetylene and olefin compounds which provides a new series of potent H$_3$ antagonists without any heteroatoms distal to the imidazole head. The high lipophilicity profiles exhibited by these compounds and high H$_3$ receptor affinity would provide improved CNS penetration profiles as well as better H$_3$ ligands for penetration of cellular membranes (i.e improved oral absorption, blood-brain barrier or cell membrane penetration profiles).

TABLE 1

Histamine H$_3$ Receptor Binding Affinities

| Example # | Structure | H$_3$ Receptor (K$_i$ nM) |
|---|---|---|
| 1 | 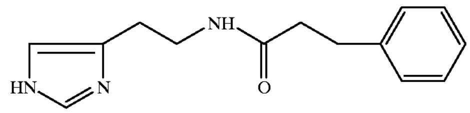 | 104 ± 14 |
| 2 | 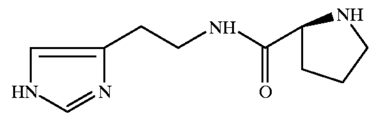 | 202 ± 2 |
| 3 | 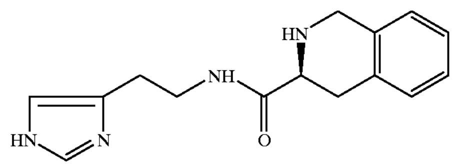 | 82.7 ± 7.7 |
| 4 | 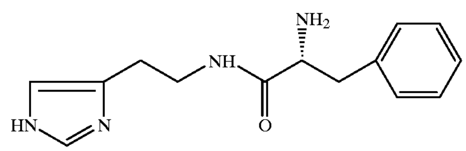 | >10,000 |
| 5 | 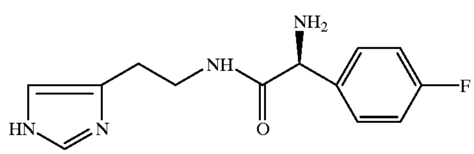 | 84.5 ± 12.8 |
| 6 | 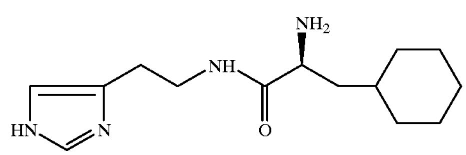 | 30.8 ± 2.1 |
| 7 | 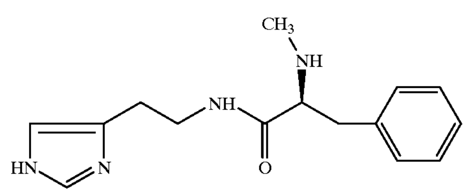 | 1650 ± 310 |
| 8 | 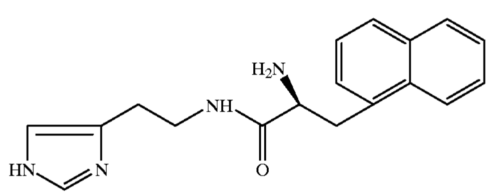 | 299 ± 82 |

TABLE 1-continued

Histamine H₃ Receptor Binding Affinities

| Example # | Structure | H₃ Receptor ($K_i$ nM) |
|---|---|---|
| 9 | (S)-2-amino-2-phenyl-N-[2-(1H-imidazol-4-yl)ethyl]acetamide | 630 ± 51 |
| 10 | (S)-2-acetamido-3-cyclohexyl-N-[2-(1H-imidazol-4-yl)ethyl]propanamide | 5485 ± 255 |
| 11 | (S)-2-amino-N-[2-(1H-imidazol-4-yl)ethyl]-4-phenylbutanamide | 10.9 ± 1.7 |
| 12 | octahydroindole-2-carboxamide N-[2-(1H-imidazol-4-yl)ethyl] | 11.1 ± 0.4 |
| 13 | (S)-2-amino-3-[4-(benzyloxy)phenyl]-N-[2-(1H-imidazol-4-yl)ethyl]propanamide | 199 ± 24 |
| 14 | (S)-2-amino-3-(benzyloxy)-N-[2-(1H-imidazol-4-yl)ethyl]propanamide | 122 ± 11 |
| 15 | (S)-2-amino-4-(benzyloxy)-N-[2-(1H-imidazol-4-yl)ethyl]-4-oxobutanamide | 81.6 ± 13.6 |
| 16 | (S)-2-amino-N-[2-(1H-imidazol-4-yl)ethyl]-3-(1H-imidazol-4-yl)propanamide | 3256 ± 457 |

TABLE 1-continued

Histamine H₃ Receptor Binding Affinities

| Example # | Structure | H₃ Receptor ($K_i$ nM) |
|---|---|---|
| 17 | 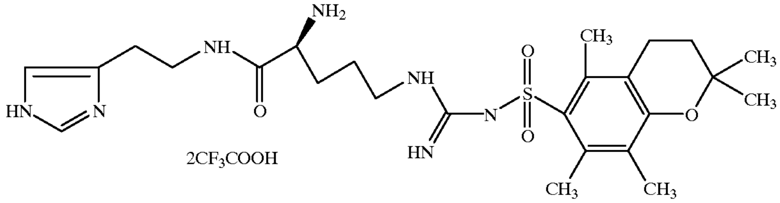 | 14 ± 3 |
| 18 | 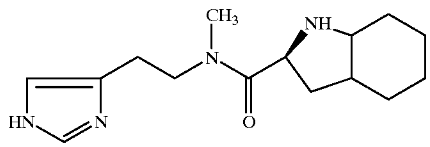 | 45 ± 11 |
| 19 | 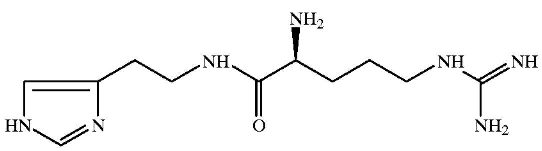 | 63 ± 1 |
| 20 | 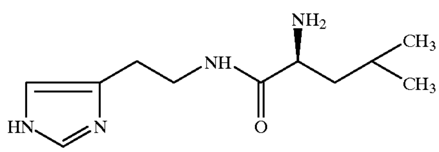 | 122 ± 37 |
| 21 | 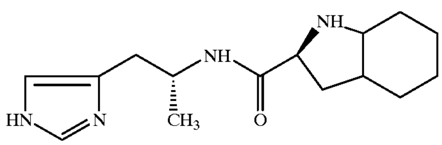 | 231 ± 15 |
| 22 | 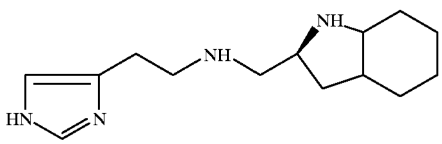 | 66 ± 4 |
| 23 | 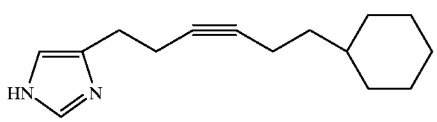 | 2.9 ± 0.2 |
| 24 | 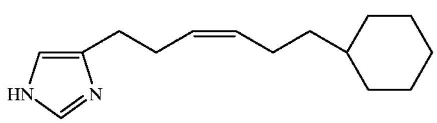 | 4.2 ± 0.6 |
| 25 | 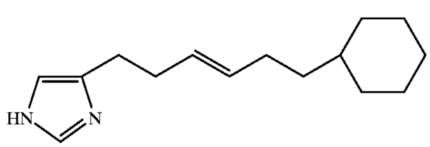 | 16 ± 2 |

TABLE 1-continued

Histamine H$_3$ Receptor Binding Affinities

| Example # | Structure | H$_3$ Receptor (K$_i$ nM) |
|---|---|---|
| 26 | 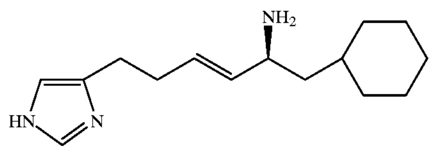 | 1.0 ± 0.1 |
| 27 | 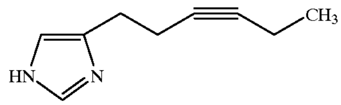 | 79 ± 22 |
| 28 | 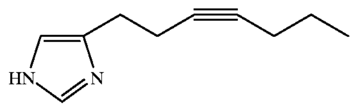 | 27 ± 7.5 |
| 29 | 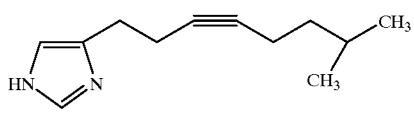 | 37 ± 1.1 |
| 30 | 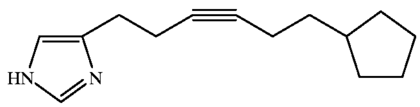 | 0.95 ± 0.3 |
| 31 | 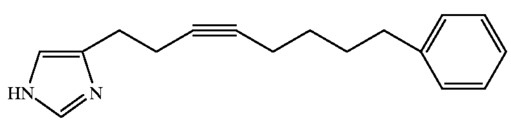 | 3.5 ± 1.0 |
| 32 | 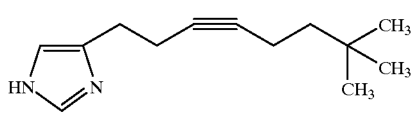 | 0.8 ± 0.4 |
| 33 | 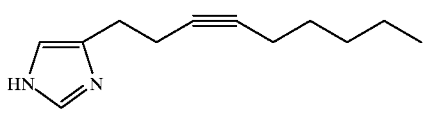 | 5.6 ± 1.0 |
| 34 | 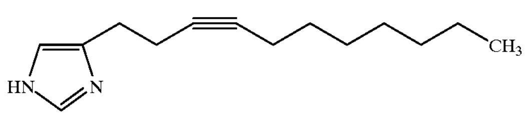 | 2.8 ± 0.7 |
| 35 | 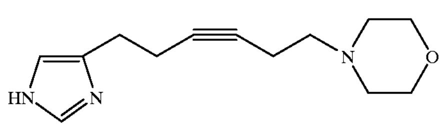 | 1212 ± 80 |
| 36 | 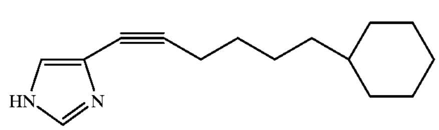 | 863 ± 139 |

TABLE 1-continued
Histamine H₃ Receptor Binding Affinities
| Example # | Structure | H₃ Receptor ($K_i$ nM) |
|---|---|---|
| 37 | 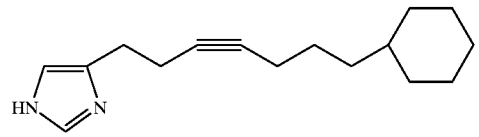 | 3.4 ± 1.7 |
| 38 | 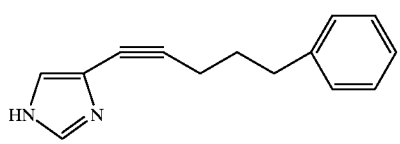 | 591 ± 36 |
| 39 | 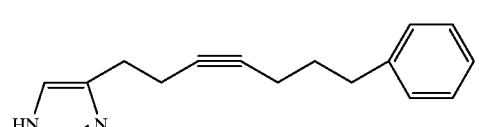 | 6.7 ± 0.6 |
| 40 | 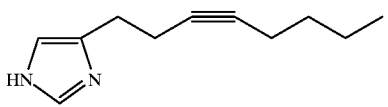 | 3.0 ± 0.2 |
| 41 | 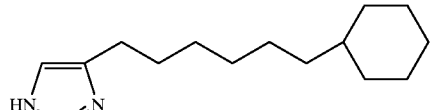 | 74.5 |
| 42 | 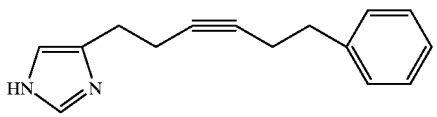 | 5.5 ± 0.02 |
| 43 | 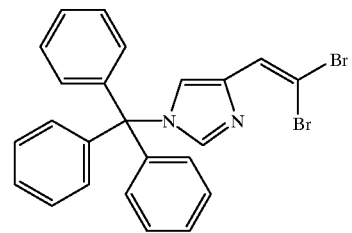 | not tested |
| 44 | 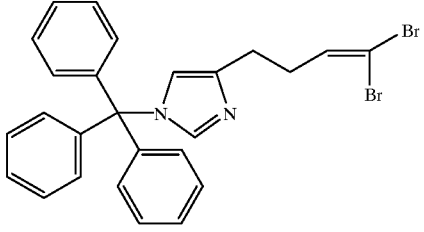 | not tested |
| 45 | 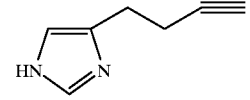 | 66 ± 5.5 |

TABLE 1-continued

Histamine H₃ Receptor Binding Affinities

| Example # | Structure | H₃ Receptor (K$_i$ nM) |
|---|---|---|
| 46 | 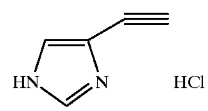 | >10,000 |
| 47 | 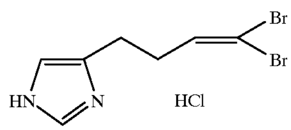 | 26 ± 9.6 |
| 48 | 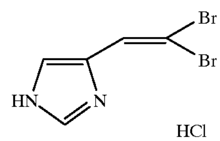 | >10,000 |

What is claimed is:

1. A compound of the formula:

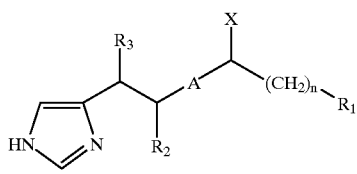

(1.0)

or a pharmaceutically acceptable salt thereof, wherein:

A is —CH=CH—, or —C≡C—;

X is H, CH₃, NH₂, NH(CH₃)₂, N(CH₃)₂, OH, OCH₃ or SH;

R₂ is a hydrogen or a methyl or ethyl group;

R₃ is a hydrogen or a methyl or ethyl group;

n is 0, 1, 2, 3, 4, 5, or 6; and

R₁ is selected from the group consisting of (a) C₁ to C₄ alky; (b) C₃ to C₈ cycloalkyl; (c) phenyl or substituted phenyl wherein the substituent may be an alkyl, halogen, amino, methoxy or cyano group; (d) decahydronapthalene; and (e) octahydroindene.

2. A compound or pharmaceutically acceptable salt thereof, as defined by claim 1, selected from the group consisting of:

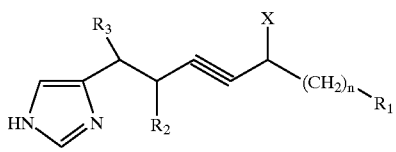

(3.0)

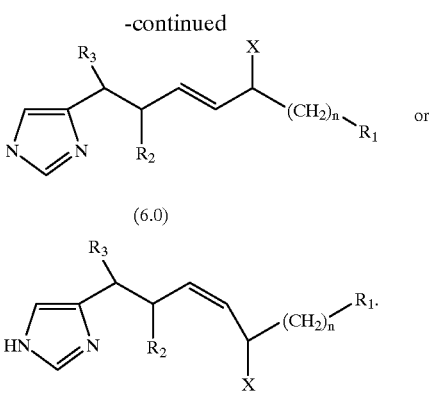

(6.0)

(7.0)

3. A compound of the formula:

(1.0)

or a pharmaceutically acceptable salt thereof, wherein:

A is —CH=CH—, or —C≡C—;

X is H, CH₃, NH₂, NH(CH₃)₂, N(CH₃)₂, OH, OCH₃ or SH;

R₂ is a hydrogen or a methyl or ethyl group;

R₃ is a hydrogen or a methyl or ethyl group;

n is 0, 1, 2, 3, 4, 5, or 6; and

R₁ is selected from the group consisting of (a) C₁ to C₄ alkyl; (b) C₃ to C₈ cycloalkyl; (c) phenyl or substituted phenyl wherein the substituent may be an alkyl, halogen, amino, methoxy or cyano group; (d) decahydronapthalene; and (e) octahydroindene.

4. A compound of the formula:

(1.0)

or a pharmaceutically acceptable salt thereof, wherein:

A is —CH=CH—, or

X is H, CH$_3$, or NH$_2$;

R$_2$ and R$_3$ are H;

n is 0, 1, 2, 3, 4, or 5; and

R$_1$ is selected from the group consisting of (a) C$_1$ to C$_4$ alkyl; (b) C$_3$ to C$_8$ cycloalkyl; (c) phenyl or substituted phenyl wherein the substituent may be an alky, halogen, amino, methoxy or cyano group; (d) decahydronapthalene; and (e) octahydroindene.

5. A compound of the formula:

(1.0)

where

A is —CH=CH—, or

X is H or NH$_2$;

R$_2$ and R$_3$ are H;

n is 1, 2 or 3; and

R$_1$ is selected from the group consisting of (a) C$_1$ to C$_4$ alkyl; (b) C$_3$ to C$_8$ cycloalkyl; (c) phenyl or substituted phenyl wherein the substituent may be an alkyl, halogen, amino, methoxy or cyano group.

6. A compound as claimed in claim 4 having the formula:

(6.0)

(7.0)

where R$_1$, R$_2$ R$_3$, n and X are as defined in claim 4.

7. A compound as claimed in claim 4 having the formula:

(3.0)

where R$_1$, R$_2$ R$_3$, n and X are as defined in claim 4.

8. A compound selected from the group consisting of (23)

4-(6-cyclohexyhex-cis-3-enyl)imidazole (24)

4-(6-cyclohexyhex-trans-3-enyl)imidazole (25)

1-cyclohexyl-6-imidazol-4-ylhex-trans-3-en-2-(S)-ylamine (26)

4-(7-methyloct-3-ynyl)imidazole (29)

4-(6-cyclopentylhex-3-ynyl)imidazole

(30)
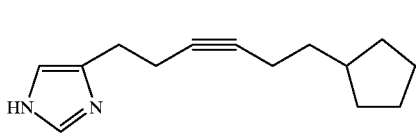

4-($^8$-phenyloct-3-ynyl)imidazole

(31)
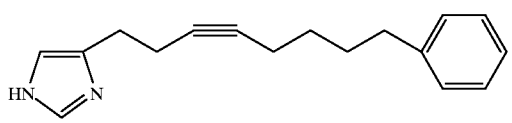

4-(7,7-dimethyloct-3-ynyl)imidazole

(32)
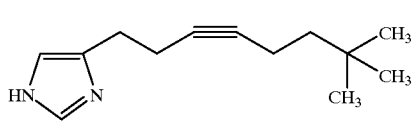

4-non-3-ynylimidazole

(33)
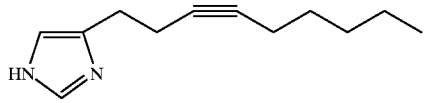

4-undec-3-ynimidpzole

(34)
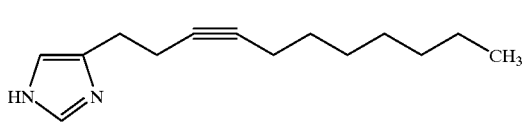

4-(7-cyclohexylhept-3-ynyl)imidazole

(37)
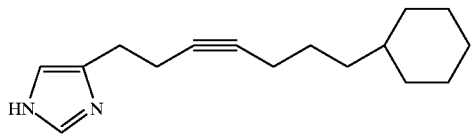

4-(7-phenylhept-3-ynyl)imidazole

(39)
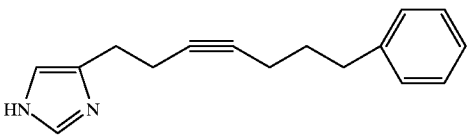

4-oct-3-ynylimidazole

(40)
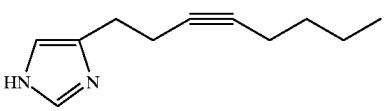

4-(6-phenylhex-cis-3-enyl)imidazole

(42)
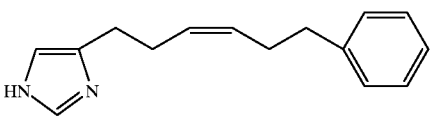

1-cyclohexyl-6-imidazol-4-ylhex-cis-3-en-2-(S)-ylamine

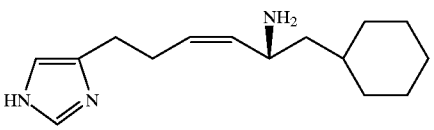

or
1-cyclohexyl-6-imidazol-4-ylhex-$^3$-yn-2-(S)-ylamine

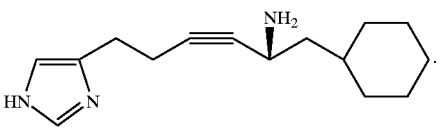

9. A compound having the structure:

(23)
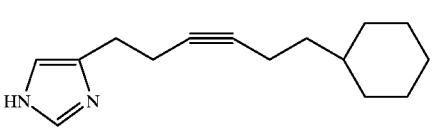

or a pharmaceutically acceptable salt thereof.
10. A compound having the structure:

(24)
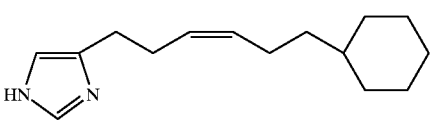

or a pharmaceutically acceptable salt thereof.

11. A compound having the structure:

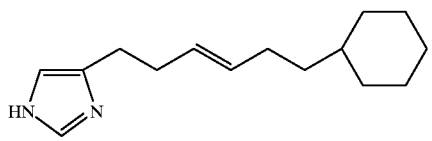
(25)

or a pharmaceutically acceptable salt thereof.

12. A compound having the structure:

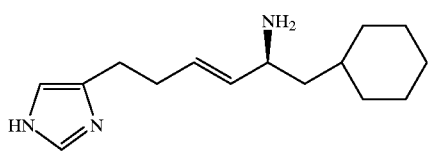
(26)

or a pharmaceutically acceptable salt thereof.

13. A compound having the structure:

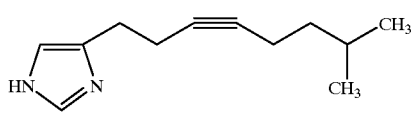
(29)

or a pharmaceutically acceptable salt thereof.

14. A compound having the structure:

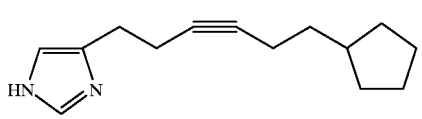
(30)

or a pharmaceutically acceptable salt thereof.

15. A compound having the structure:

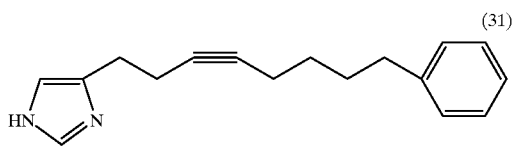
(31)

or a pharmaceutically acceptable salt thereof.

16. A compound having the structure:

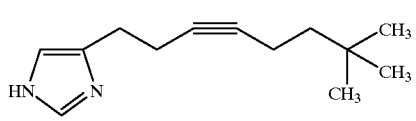
(32)

or a pharmaceutically acceptable salt thereof.

17. A compound having the structure:

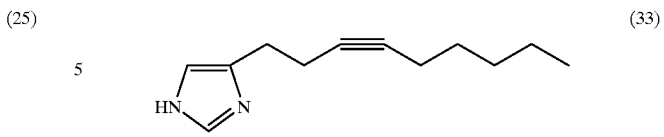
(33)

or a pharmaceutically acceptable salt thereof.

18. A compound having the structure:

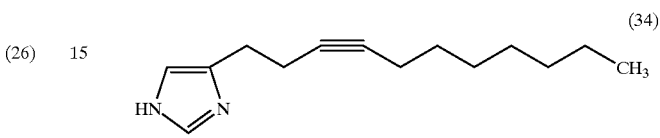
(34)

or a pharmaceutically acceptable salt thereof.

19. A compound having the structure:

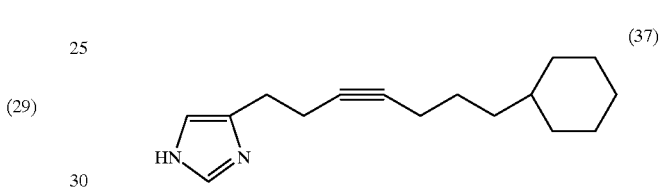
(37)

or a pharmaceutically acceptable salt thereof.

20. A compound having the structure:

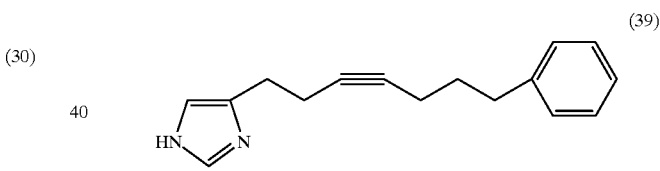
(39)

or a pharmaceutically acceptable salt thereof.

21. A compound having the structure:

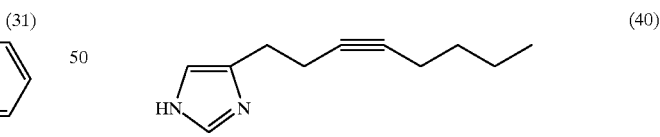
(40)

or a pharmaceutically acceptable salt thereof.

22. A compound having the structure:

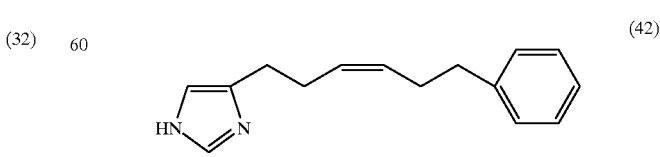
(42)

or a pharmaceutically acceptable salt thereof.

23. A compound having the structure:
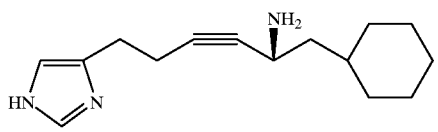
or a pharmaceutically acceptable salt thereof.
24. A pharmaceutical composition comprising a compound of claim 1 and a pharmaceutically acceptable carrier.
* * * * *

UNITED STATES PATENT AND TRADEMARK OFFICE
CERTIFICATE OF CORRECTION

PATENT NO. : 6,166,060
DATED : December 26, 2000
INVENTOR(S) : Phillips et al.

It is certified that error appears in the above-identified patent and that said Letters Patent is hereby corrected as shown below:

Title page,
Item [63], under Related U.S. Applications Data, before May 30, 1995, please insert -- filed --.

Column 2,
Line 30, please delete "a $H_3$" and insert -- an $H_3$ --
Line 61, please delete "a $H_3$" and insert -- an $H_3$ --

Column 7,
Line 20, please delete "consisting of of" and insert -- consisting of --

Column 14,
Under Scheme 1, please delete "C1" and insert -- BOC --

Column 22,
Line 33, please delete "N-BOC" and insert -- n-BOC --

Column 23,
Line 38, please delete "hydroisoquinolyltormamide" and insert
-- hydroisoquinolylformamide --

Column 28,
Line 57, please delete "Preparation of N-PMC-(L)-arginine-histamine amide (2-(S)-amino-N-(2-imidazol-4yiethyl)-5-((imino(((2,2,5,7,8-pentamethylchroman-6-yl)sulfonyl)amino)methyl)amino)pentanamide)" and insert -- Preparation of N-PMC-(L)-arginine-histamine amide (2-(S)-amino-N-(2-imidazol-4ylethyl)-5-((imino (((2,2,5,7,8-pentamethylchroman-6-yl)sulfonyl)amino)methyl)amino)pentanamide) --

Column 35,
Line 51, please delete "MEOH" and insert -- MeOH --

Column 37,
Line 1, please delete "NMR (300 $MH_z$, $CDC_{13}$):" and insert -- NMR (300 $MH_z$, $CHCl_3$) --

UNITED STATES PATENT AND TRADEMARK OFFICE
CERTIFICATE OF CORRECTION

PATENT NO.    : 6,166,060
DATED         : December 26, 2000
INVENTOR(S)   : Phillips et al.

It is certified that error appears in the above-identified patent and that said Letters Patent is hereby corrected as shown below:

Column 57,
Line 54, please delete "and (e) octahydroindene." and insert -- and (e) octahydroindane. --

Column 60,
Line 15, please delete "A compound selected from the group consisting of" and insert -- A compound selected from the group consisting of 4-(6-cycloheylhex-3-ynyl) imidazole --

Signed and Sealed this

Sixth Day of August, 2002

Attest:

Attesting Officer

JAMES E. ROGAN
Director of the United States Patent and Trademark Office